(12) United States Patent
Hampikian

(10) Patent No.: US 8,927,213 B2
(45) Date of Patent: Jan. 6, 2015

(54) REFERENCE MARKERS FOR BIOLOGICAL SAMPLES

(76) Inventor: Greg Hampikian, Boise, ID (US)

(*) Notice: Subject to any disclaimer, the term of this patent is extended or adjusted under 35 U.S.C. 154(b) by 240 days.

(21) Appl. No.: 13/274,592

(22) Filed: Oct. 17, 2011

(65) Prior Publication Data

US 2012/0115154 A1     May 10, 2012

Related U.S. Application Data

(60) Continuation-in-part of application No. 12/941,860, filed on Nov. 8, 2010, now abandoned, which is a division of application No. 11/024,293, filed on Dec. 23, 2004, now abandoned.

(51) Int. Cl.
    *C07H 21/04*     (2006.01)
    *C12Q 1/68*     (2006.01)

(52) U.S. Cl.
    CPC ........................................ *C12Q 1/68* (2013.01)
    USPC ......... 435/6.1; 435/6.11; 435/6.12; 435/91.1; 435/91.2

(58) Field of Classification Search
None
See application file for complete search history.

(56) References Cited

U.S. PATENT DOCUMENTS 6,312,911 B1 * 11/2001 Bancroft et al. ............. 435/6.11
7,396,646 B2 * 7/2008 Quinlan et al. .............. 435/6.14
2010/0092948 A1 * 4/2010 Davis et al. ....................... 435/6

OTHER PUBLICATIONS

Hampikian et al. Pacific Symposium on Biocomuting, vol. 12, pp. 355-366, 2007.*

* cited by examiner

*Primary Examiner* — Jeanine A Goldberg
(74) *Attorney, Agent, or Firm* — Whitham, Curtis, Christofferson & Cook, P.C.

(57) ABSTRACT

DNA oligomers comprising sequences that are absent from the genome of one or more organisms of interest are used as reference markers (RMs). The RMs are added to biological samples to "tag" and subsequently identify the samples as authentic and to distinguish tagged samples from samples obtained without said markers, for example, in forensic, medical, legal and other applications.

8 Claims, 7 Drawing Sheets

Figure 1A:
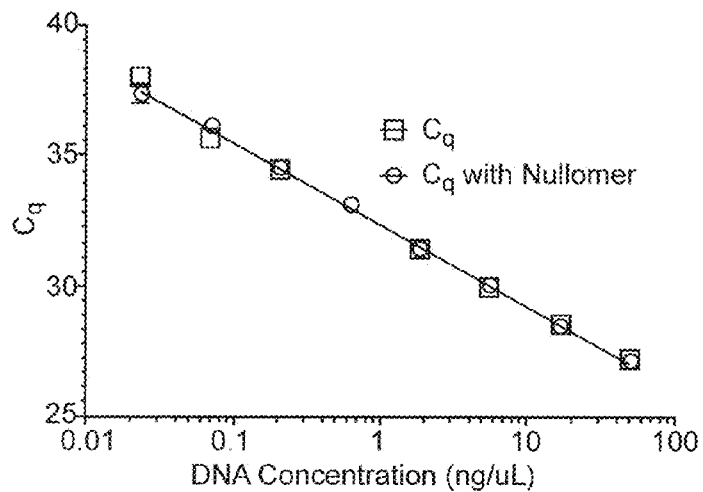

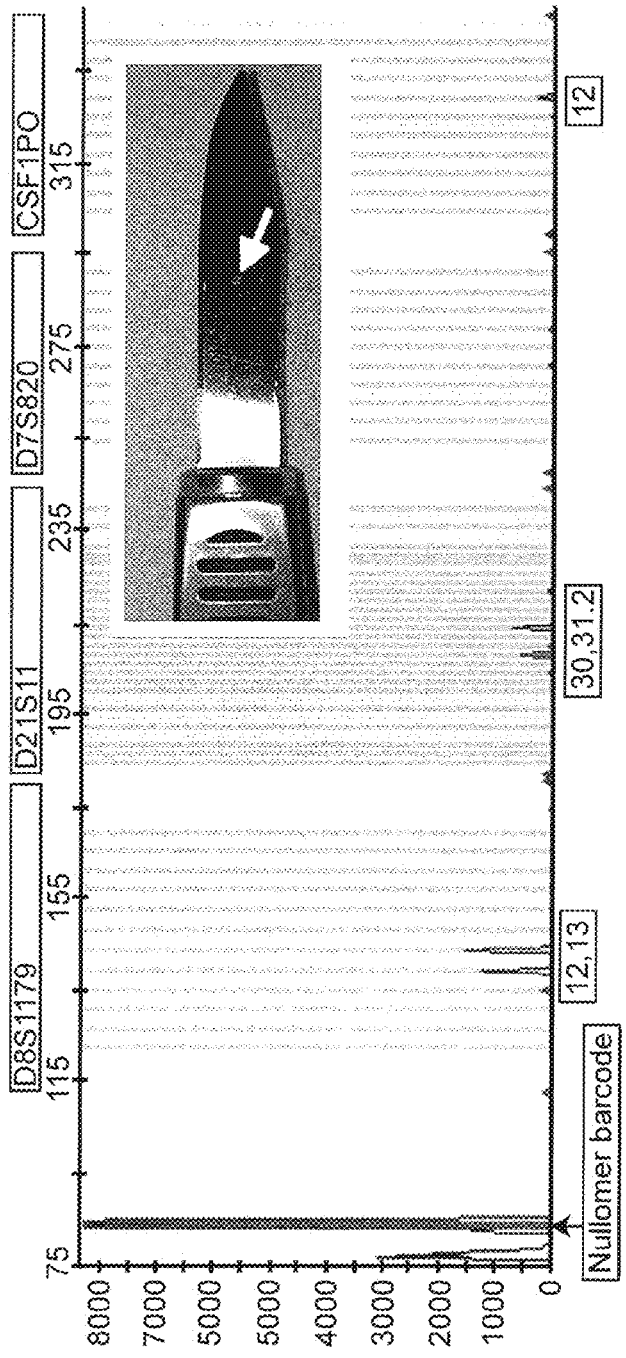
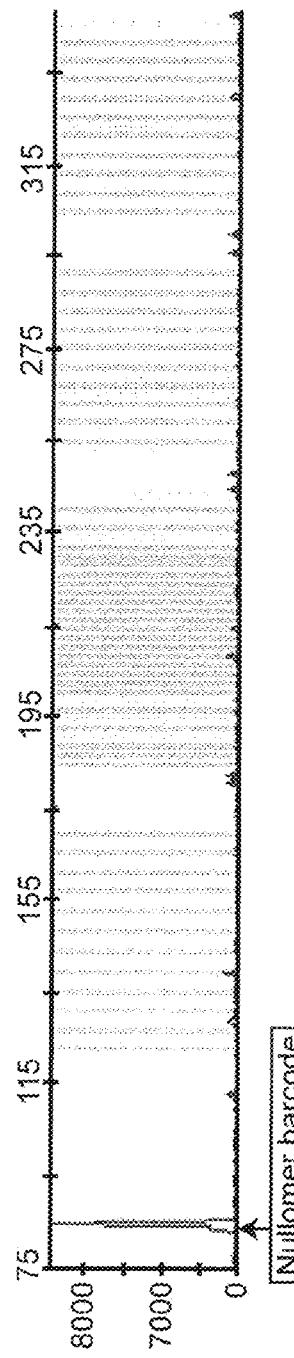
Figure 7A
Figure 7B

SEQUENCE LISTING

```
<160> NUMBER OF SEQ ID NOS: 377

<210> SEQ ID NO 1
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 1
aacttcgcta gcggg                                                          15

<210> SEQ ID NO 2
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 2
accctaaggc gcgta                                                          15

<210> SEQ ID NO 3
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 3
accgggctag tcgta                                                          15

<210> SEQ ID NO 4
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 4
acctagttcg cgcta                                                          15

<210> SEQ ID NO 5
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 5
acgatagtct aacgc                                                          15

<210> SEQ ID NO 6
<211> LENGTH: 15
<212> TYPE: DNA
```

```
<213> ORGANISM: Artificial Sequence
<220> FEATURE:
<223> OTHER INFORMATION: synthetic oligonucleotide

<400> SEQUENCE: 6
acgcgaccgc taagt                                                    15

<210> SEQ ID NO 7
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 7
acgcgcgact agtaa                                                    15

<210> SEQ ID NO 8
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 8
acggactagc gcgct                                                    15

<210> SEQ ID NO 9
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 9
acggttaggc ccgta                                                    15

<210> SEQ ID NO 10
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 10
acgtagggtt acgcg                                                    15

<210> SEQ ID NO 11
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 11
acgttagtac gccga                                                    15

<210> SEQ ID NO 12
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 12
actaacgtct cgcgc                                                    15
```

<210> SEQ ID NO 13
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 13
actacgcgta gggtc                                                        15

<210> SEQ ID NO 14
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 14
actagcggtc cgacg                                                        15

<210> SEQ ID NO 15
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 15
actagtacgc tcccg                                                        15

<210> SEQ ID NO 16
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 16
actagtcgcg gctac                                                        15

<210> SEQ ID NO 17
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 17
actagtcggt acccg                                                        15

<210> SEQ ID NO 18
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 18
acttacgccc tatcg                                                        15

<210> SEQ ID NO 19
<211> LENGTH: 15
<212> TYPE: DNA
<213> ORGANISM: Artificial Sequence
<220> FEATURE:

```
<223> OTHER INFORMATION: synthetic oligonucleotide

<400> SEQUENCE: 19
acttacgcgg tccta                                              15

<210> SEQ ID NO 20
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 20
acttagcggt cgcgt                                              15

<210> SEQ ID NO 21
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 21
agcgcgctag tccgt                                              15

<210> SEQ ID NO 22
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 22
agctaggcgc gttac                                              15

<210> SEQ ID NO 23
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 23
aggcgcgaac tagta                                              15

<210> SEQ ID NO 24
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 24
agtctaaccg gcgta                                              15

<210> SEQ ID NO 25
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 25
agttaggccc gacgc                                              15
```

```
<210> SEQ ID NO 26
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 26
atactagacc gctcg                                                    15

<210> SEQ ID NO 27
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 27
atactagcgt cggac                                                    15

<210> SEQ ID NO 28
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 28
atagccgcgg tccta                                                    15

<210> SEQ ID NO 29
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 29
atagcgcgtt aggac                                                    15

<210> SEQ ID NO 30
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 30
atccgaccta gcgta                                                    15

<210> SEQ ID NO 31
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 31
attaggcccg cgatc                                                    15

<210> SEQ ID NO 32
<211> LENGTH: 15
<212> TYPE: DNA
<213> ORGANISM: Artificial Sequence
<220> FEATURE:
<223> OTHER INFORMATION: synthetic oligonucleotide
```

```
<400> SEQUENCE: 32
catcggacta gtacc                                                    15

<210> SEQ ID NO 33
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 33
ccaacctacg cgtag                                                    15

<210> SEQ ID NO 34
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 34
ccacgggcta gcgta                                                    15

<210> SEQ ID NO 35
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 35
ccatacgcct agtcg                                                    15

<210> SEQ ID NO 36
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 36
ccccgtacta gcgga                                                    15

<210> SEQ ID NO 37
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 37
ccccgtagcg aactc                                                    15

<210> SEQ ID NO 38
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 38
cccgacttaa gagcg                                                    15

<210> SEQ ID NO 39
<211> LENGTH: 15
```

<212> TYPE: DNA
<213> ORGANISM: Artificial Sequence
<220> FEATURE:
<223> OTHER INFORMATION: synthetic oligonucleotide

<400> SEQUENCE: 39
cccgcatacg actag                                                    15

<210> SEQ ID NO 40
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 40
cccgcgttgt acgta                                                    15

<210> SEQ ID NO 41
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 41
cccgctagcg aagtt                                                    15

<210> SEQ ID NO 42
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 42
cccggaacta gcgta                                                    15

<210> SEQ ID NO 43
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 43
cccgtatcgc gctag                                                    15

<210> SEQ ID NO 44
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 44
cccgttacgc gacta                                                    15

<210> SEQ ID NO 45
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 45
ccctaacgcg tacta                                                    15

<210> SEQ ID NO 46
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 46
ccctacgtcg tagcg                                                    15

<210> SEQ ID NO 47
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 47
ccctagcgac ccgta                                                    15

<210> SEQ ID NO 48
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 48
ccctatacgc cgtag                                                    15

<210> SEQ ID NO 49
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 49
ccgcgtaggg actag                                                    15

<210> SEQ ID NO 50
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 50
ccgggcgtag ctaac                                                    15

<210> SEQ ID NO 51
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 51
ccggtgtact aacgc                                                    15

<210> SEQ ID NO 52
<211> LENGTH: 15
<212> TYPE: DNA
<213> ORGANISM: Artificial Sequence

```
<220> FEATURE:
<223> OTHER INFORMATION: synthetic oligonucleotide

<400> SEQUENCE: 52
ccgtactaag ggcgc                                                    15

<210> SEQ ID NO 53
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 53
ccgtactacg gctta                                                    15

<210> SEQ ID NO 54
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 54
cctaggttcc gcgta                                                    15

<210> SEQ ID NO 55
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 55
cctagtacga cccgc                                                    15

<210> SEQ ID NO 56
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 56
cctagtacgt tacga                                                    15

<210> SEQ ID NO 57
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 57
cctagtatac gcccg                                                    15

<210> SEQ ID NO 58
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 58
cctagtcgcg tagac                                                    15
```

```
<210> SEQ ID NO 59
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 59
ccttagacgc ggtcg                                                    15

<210> SEQ ID NO 60
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 60
ccttagtgcg acccg                                                    15

<210> SEQ ID NO 61
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 61
cgaatctagg cggac                                                    15

<210> SEQ ID NO 62
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 62
cgaccgcgtc taagg                                                    15

<210> SEQ ID NO 63
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 63
cgactaagca taccg                                                    15

<210> SEQ ID NO 64
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 64
cgactaggcg tatgg                                                    15

<210> SEQ ID NO 65
<211> LENGTH: 15
<212> TYPE: DNA
<213> ORGANISM: Artificial Sequence
<220> FEATURE:
<223> OTHER INFORMATION: synthetic oligonucleotide
```

```
<400> SEQUENCE: 65
cgagcggtct agtat                                               15

<210> SEQ ID NO 66
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 66
cgatagggcg taagt                                               15

<210> SEQ ID NO 67
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 67
cgatagtcta acgcg                                               15

<210> SEQ ID NO 68
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 68
cgatcggtaa cctag                                               15

<210> SEQ ID NO 69
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 69
cgcctagttc cgtac                                               15

<210> SEQ ID NO 70
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 70
cgcgaactta gttag                                               15

<210> SEQ ID NO 71
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 71
cgcgcgtatt agacc                                               15

<210> SEQ ID NO 72
```

```
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 72
cgcggaacgt cccta                                                      15

<210> SEQ ID NO 73
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 73
cgcggaagtc tagta                                                      15

<210> SEQ ID NO 74
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 74
cgcggacgct agtta                                                      15

<210> SEQ ID NO 75
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 75
cgcggtccgt actag                                                      15

<210> SEQ ID NO 76
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 76
cgcgtaaccc tacgt                                                      15

<210> SEQ ID NO 77
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 77
cgcgtacgat agtcc                                                      15

<210> SEQ ID NO 78
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 78
```
cgcgtagatt agtcc                                                15

<210> SEQ ID NO 79
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 79
cgcgtagcgg actta                                                15

<210> SEQ ID NO 80
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 80
cgcgtaggct agttc                                                15

<210> SEQ ID NO 81
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 81
cgcgtatcgg gctag                                                15

<210> SEQ ID NO 82
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 82
cgcgttagac tatcg                                                15

<210> SEQ ID NO 83
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 83
cgctacgacg taggg                                                15

<210> SEQ ID NO 84
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 84
cgctacgtag taacg                                                15

<210> SEQ ID NO 85
<211> LENGTH: 15
<212> TYPE: DNA

```
<213> ORGANISM: Artificial Sequence
<220> FEATURE:
<223> OTHER INFORMATION: Synthetic oligonucleotide

<400> SEQUENCE: 85
cgctagtacg cgaac                                                    15

<210> SEQ ID NO 86
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 86
cgctcttaag tcggg                                                    15

<210> SEQ ID NO 87
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 87
cggacctacg cgtaa                                                    15

<210> SEQ ID NO 88
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 88
cgggactatc ctacg                                                    15

<210> SEQ ID NO 89
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 89
cgggagcgta ctagt                                                    15

<210> SEQ ID NO 90
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 90
cgggcgtata ctagg                                                    15

<210> SEQ ID NO 91
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 91
cgggggatcg tacta                                                    15
```

<210> SEQ ID NO 92
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 92
cggggtacga tctag                                                    15

<210> SEQ ID NO 93
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 93
cgggtaccga ctagt                                                    15

<210> SEQ ID NO 94
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 94
cgggtcccgc taata                                                    15

<210> SEQ ID NO 95
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 95
cgggtcgcac taagg                                                    15

<210> SEQ ID NO 96
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 96
cggtacgtac tagac                                                    15

<210> SEQ ID NO 97
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 97
cggtaggacg cccta                                                    15

<210> SEQ ID NO 98
<211> LENGTH: 15
<212> TYPE: DNA
<213> ORGANISM: Artificial Sequence
<220> FEATURE:

<223> OTHER INFORMATION: Synthetic oligonucleotide

<400> SEQUENCE: 98
cggtatgctt agtcg                                                      15

<210> SEQ ID NO 99
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 99
cggtcgtact aaccg                                                      15

<210> SEQ ID NO 100
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 100
cggtctacgc gtaac                                                      15

<210> SEQ ID NO 101
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 101
cggtcttacg cgtta                                                      15

<210> SEQ ID NO 102
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 102
cggtgcgtag cccta                                                      15

<210> SEQ ID NO 103
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 103
cggttagtac gaccg                                                      15

<210> SEQ ID NO 104
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 104
cgtaagaccg gaccc                                                      15

```
<210> SEQ ID NO 105
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 105
cgtacgcgga ctagc                                                    15

<210> SEQ ID NO 106
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 106
cgtacggcta accta                                                    15

<210> SEQ ID NO 107
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 107
cgtagcgtac gctag                                                    15

<210> SEQ ID NO 108
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 108
cgtaggaccg ttaag                                                    15

<210> SEQ ID NO 109
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 109
cgtaggacgg cctaa                                                    15

<210> SEQ ID NO 110
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 110
cgtaggatag tcccg                                                    15

<210> SEQ ID NO 111
<211> LENGTH: 15
<212> TYPE: DNA
<213> ORGANISM: Artificial Sequence
<220> FEATURE:
<223> OTHER INFORMATION: Synthetic oligonucleotide
```

<400> SEQUENCE: 111
cgtagggcgt actta                                                    15

<210> SEQ ID NO 112
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 112
cgtagtcccc gctag                                                    15

<210> SEQ ID NO 113
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 113
cgtccgacta tagag                                                    15

<210> SEQ ID NO 114
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 114
cgtcgctaat ctaag                                                    15

<210> SEQ ID NO 115
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 115
cgtcggaccg ctagt                                                    15

<210> SEQ ID NO 116
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 116
cgtcgtacta gggtc                                                    15

<210> SEQ ID NO 117
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 117
cgtctaacta accgc                                                    15

<210> SEQ ID NO 118
<211> LENGTH: 15

```
<212> TYPE: DNA
<213> ORGANISM: Artificial Sequence
<220> FEATURE:
<223> OTHER INFORMATION: Synthetic oligonucleotide

<400> SEQUENCE: 118
cgtctactag tcgga                                                    15

<210> SEQ ID NO 119
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 119
cgttactacg tagcg                                                    15

<210> SEQ ID NO 120
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 120
cgttagtacg cggtc                                                    15

<210> SEQ ID NO 121
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 121
cgtttagcgg tctac                                                    15

<210> SEQ ID NO 122
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 122
ctaactaagt tcgcg                                                    15

<210> SEQ ID NO 123
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 123
ctacgcgtag gttgg                                                    15

<210> SEQ ID NO 124
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 124
```

```
ctacggcgta taggg                                            15

<210> SEQ ID NO 125
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 125
ctacggggcg tagta                                            15

<210> SEQ ID NO 126
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 126
ctacgggtag accga                                            15

<210> SEQ ID NO 127
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 127
ctagacgccc gtata                                            15

<210> SEQ ID NO 128
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 128
ctagatcgta ccccg                                            15

<210> SEQ ID NO 129
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 129
ctagcccgat acgcg                                            15

<210> SEQ ID NO 130
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 130
ctagcgcgat acggg                                            15

<210> SEQ ID NO 131
<211> LENGTH: 15
<212> TYPE: DNA
<213> ORGANISM: Artificial Sequence
```

<220> FEATURE:
<223> OTHER INFORMATION: Synthetic oligonucleotide

<400> SEQUENCE: 131
ctagcgggga ctacg                                                    15

<210> SEQ ID NO 132
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 132
ctagcgtacg ctacg                                                    15

<210> SEQ ID NO 133
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 133
ctaggcgcga tatcc                                                    15

<210> SEQ ID NO 134
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 134
ctaggttacc gatcg                                                    15

<210> SEQ ID NO 135
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 135
ctagtaactc gcggc                                                    15

<210> SEQ ID NO 136
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 136
ctagtacgga ccgcg                                                    15

<210> SEQ ID NO 137
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 137
ctagtcccta cgcgg                                                    15

<210> SEQ ID NO 138
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 138
ctagtcggac cgtac                                                        15

<210> SEQ ID NO 139
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 139
ctagtcggta cgggc                                                        15

<210> SEQ ID NO 140
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 140
ctagtcgtat gcggg                                                        15

<210> SEQ ID NO 141
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 141
ctagtcgtcc gggta                                                        15

<210> SEQ ID NO 142
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 142
ctctatagtc ggacg                                                        15

<210> SEQ ID NO 143
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 143
cttaacggtc ctacg                                                        15

<210> SEQ ID NO 144
<211> LENGTH: 15
<212> TYPE: DNA
<213> ORGANISM: Artificial Sequence
<220> FEATURE:
<223> OTHER INFORMATION: Synthetic oligonucleotide -continued

```
<400> SEQUENCE: 144
cttagattag cgacg                                              15

<210> SEQ ID NO 145
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 145
cttagggcgt tacgc                                              15

<210> SEQ ID NO 146
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 146
cttagtcgcg tccta                                              15

<210> SEQ ID NO 147
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 147
gaactagcct acgcg                                              15

<210> SEQ ID NO 148
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 148
gaccctacgc gtagt                                              15

<210> SEQ ID NO 149
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 149
gaccctagta cgacg                                              15

<210> SEQ ID NO 150
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 150
gaccgcgtac taacg                                              15

<210> SEQ ID NO 151
```

```
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 151
gagttcgcta cgggg                                                    15

<210> SEQ ID NO 152
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 152
gatcgcgggc ctaat                                                    15

<210> SEQ ID NO 153
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 153
gcccgactta gcgta                                                    15

<210> SEQ ID NO 154
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 154
gcccgtaccg actag                                                    15

<210> SEQ ID NO 155
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 155
gccgcgagtt actag                                                    15

<210> SEQ ID NO 156
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 156
gcgcccttag tacgg                                                    15

<210> SEQ ID NO 157
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 157
```

```
gcgcgagacg ttagt                                          15

<210> SEQ ID NO 158
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 158
gcgcgatagg tctaa                                          15

<210> SEQ ID NO 159
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 159
gcgcgtccta tcaac                                          15

<210> SEQ ID NO 160
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 160
gcgcttagac gggta                                          15

<210> SEQ ID NO 161
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 161
gcgggtcgta ctagg                                          15

<210> SEQ ID NO 162
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 162
gcggttagtt agacg                                          15

<210> SEQ ID NO 163
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 163
gcgtaacgcc ctaag                                          15

<210> SEQ ID NO 164
<211> LENGTH: 15
<212> TYPE: DNA
```

```
<213> ORGANISM: Artificial Sequence
<220> FEATURE:
<223> OTHER INFORMATION: Synthetic oligonucleotide

<400> SEQUENCE: 164
gcgtccgtag tctac                                                      15

<210> SEQ ID NO 165
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 165
gcgtcgggcc taact                                                      15

<210> SEQ ID NO 166
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 166
gcgttagact atcgt                                                      15

<210> SEQ ID NO 167
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 167
gcgttagtac accgg                                                      15

<210> SEQ ID NO 168
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 168
gctagtccgc gtacg                                                      15

<210> SEQ ID NO 169
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 169
ggactaatct acgcg                                                      15

<210> SEQ ID NO 170
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 170
ggactatcgt acgcg                                                      15
```

<210> SEQ ID NO 171
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 171
ggatatcgcg cctag                                              15

<210> SEQ ID NO 172
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 172
ggccgcgtat agata                                              15

<210> SEQ ID NO 173
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 173
gggcctaagt cgcga                                              15

<210> SEQ ID NO 174
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 174
gggctagtac gcgta                                              15

<210> SEQ ID NO 175
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 175
gggtacctaa cgcga                                              15

<210> SEQ ID NO 176
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 176
gggtccggtc ttacg                                              15

<210> SEQ ID NO 177
<211> LENGTH: 15
<212> TYPE: DNA
<213> ORGANISM: Artificial Sequence
<220> FEATURE:

<223> OTHER INFORMATION: Synthetic oligonucleotide

<400> SEQUENCE: 177
ggtactagtc cgatg                                                    15

<210> SEQ ID NO 178
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 178
ggtcgcgcta ctaga                                                    15

<210> SEQ ID NO 179
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 179
ggtctaatac gcgcg                                                    15

<210> SEQ ID NO 180
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 180
ggttacgcgg accta                                                    15

<210> SEQ ID NO 181
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 181
gtaacgcgcc tagct                                                    15

<210> SEQ ID NO 182
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 182
gtaactaacc gcgga                                                    15

<210> SEQ ID NO 183
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 183
gtaagacggg tcgca                                                    15

```
<210> SEQ ID NO 184
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 184
gtacggaact aggcg                                                    15

<210> SEQ ID NO 185
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 185
gtacgggcgc tagac                                                    15

<210> SEQ ID NO 186
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 186
gtacggtccg actag                                                    15

<210> SEQ ID NO 187
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 187
gtagaccgct aaacg                                                    15

<210> SEQ ID NO 188
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 188
gtagactacg gacgc                                                    15

<210> SEQ ID NO 189
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 189
gtagccgcga ctagt                                                    15

<210> SEQ ID NO 190
<211> LENGTH: 15
<212> TYPE: DNA
<213> ORGANISM: Artificial Sequence
<220> FEATURE:
<223> OTHER INFORMATION: Synthetic oligonucleotide
```

<400> SEQUENCE: 190
gtccgacgct agtat                                                        15

<210> SEQ ID NO 191
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 191
gtccgcctag attcg                                                        15

<210> SEQ ID NO 192
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 192
gtccgcgcta cgtta                                                        15

<210> SEQ ID NO 193
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 193
gtcctaacgc gctat                                                        15

<210> SEQ ID NO 194
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 194
gtcggtacgc ctaga                                                        15

<210> SEQ ID NO 195
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 195
gtctacgcga ctagg                                                        15

<210> SEQ ID NO 196
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 196
gtctagaccg cgtta                                                        15

<210> SEQ ID NO 197
<211> LENGTH: 15

```
<212> TYPE: DNA
<213> ORGANISM: Artificial Sequence
<220> FEATURE:
<223> OTHER INFORMATION: Synthetic oligonucleotide

<400> SEQUENCE: 197
gtctagcgcc cgtac                                                    15

<210> SEQ ID NO 198
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 198
gtctagtacg taccg                                                    15

<210> SEQ ID NO 199
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 199
gttacgcgta gaccg                                                    15

<210> SEQ ID NO 200
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 200
gttagacggc gcgta                                                    15

<210> SEQ ID NO 201
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 201
gttagctacg cccgg                                                    15

<210> SEQ ID NO 202
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 202
gttcgcgtac tagcg                                                    15

<210> SEQ ID NO 203
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 203
```

```
gttgatagga cgcgc                                                    15
```

<210> SEQ ID NO 204
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 204

```
taacgcggtc tagac                                                    15
```

<210> SEQ ID NO 205
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 205

```
taacgcgtaa gaccg                                                    15
```

<210> SEQ ID NO 206
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 206

```
taacgtagcg cggac                                                    15
```

<210> SEQ ID NO 207
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 207

```
taacgtcgcg ttaga                                                    15
```

<210> SEQ ID NO 208
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 208

```
taactagcgt ccgcg                                                    15
```

<210> SEQ ID NO 209
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 209

```
taagccgtag tacgg                                                    15
```

<210> SEQ ID NO 210
<211> LENGTH: 15
<212> TYPE: DNA
<213> ORGANISM: Artificial Sequence

```
<220> FEATURE:
<223> OTHER INFORMATION: Synthetic oligonucleotide

<400> SEQUENCE: 210
taagctacgg gcgta                                                    15

<210> SEQ ID NO 211
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 211
taagtacgcc ctacg                                                    15

<210> SEQ ID NO 212
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 212
taagtccgct acgcg                                                    15

<210> SEQ ID NO 213
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 213
tacccggacg actag                                                    15

<210> SEQ ID NO 214
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 214
tacccgtcta agcgc                                                    15

<210> SEQ ID NO 215
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 215
tacgactagc ccggt                                                    15

<210> SEQ ID NO 216
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 216
tacgcccgta gctta                                                    15
```

<210> SEQ ID NO 217
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 217
tacgccggtt agact                                                    15

<210> SEQ ID NO 218
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 218
tacgcctagg ggcga                                                    15

<210> SEQ ID NO 219
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 219
tacgcgccgt ctaac                                                    15

<210> SEQ ID NO 220
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 220
tacgcgcctt agggt                                                    15

<210> SEQ ID NO 221
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 221
tacgcggaac ctagg                                                    15

<210> SEQ ID NO 222
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 222
tacgcgtact agccc                                                    15

<210> SEQ ID NO 223
<211> LENGTH: 15
<212> TYPE: DNA
<213> ORGANISM: Artificial Sequence
<220> FEATURE:
<223> OTHER INFORMATION: Synthetic oligonucleotide

```
<400> SEQUENCE: 223
tacgctaagt cgggc                                                   15

<210> SEQ ID NO 224
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 224
tacgctagcc cgtgg                                                   15

<210> SEQ ID NO 225
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 225
tacgctaggt cggat                                                   15

<210> SEQ ID NO 226
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 226
tacgctagtt ccggg                                                   15

<210> SEQ ID NO 227
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 227
tacgggccta accgt                                                   15

<210> SEQ ID NO 228
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 228
tacgggcgtc tagta                                                   15

<210> SEQ ID NO 229
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 229
tacggggcgt cccta                                                   15

<210> SEQ ID NO 230
```

```
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 230
tacgggtcgc taggg                                                    15

<210> SEQ ID NO 231
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 231
tacgtacaac gcggg                                                    15

<210> SEQ ID NO 232
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 232
tactacgccc cgtag                                                    15

<210> SEQ ID NO 233
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 233
tactagacgc ccgta                                                    15

<210> SEQ ID NO 234
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 234
tactagactt ccgcg                                                    15

<210> SEQ ID NO 235
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 235
tactaggcga ctcga                                                    15

<210> SEQ ID NO 236
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 236
```

```
tactagttcg cgcct                                                    15

<210> SEQ ID NO 237
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 237
tacttaggtc cgcga                                                    15

<210> SEQ ID NO 238
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 238
tagacctagc gcgga                                                    15

<210> SEQ ID NO 239
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 239
tagcgcgaac taggt                                                    15

<210> SEQ ID NO 240
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 240
tagcggacgg tccta                                                    15

<210> SEQ ID NO 241
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 241
taggaccgcg gctat                                                    15

<210> SEQ ID NO 242
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 242
taggaccgcg taagt                                                    15

<210> SEQ ID NO 243
<211> LENGTH: 15
<212> TYPE: DNA
```

```
<213> ORGANISM: Artificial Sequence
<220> FEATURE:
<223> OTHER INFORMATION: Synthetic oligonucleotide

<400> SEQUENCE: 243
taggaccgtc cgcta                                                    15

<210> SEQ ID NO 244
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 244
taggacgcga ctaag                                                    15

<210> SEQ ID NO 245
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 245
tagggacgcc ccgta                                                    15

<210> SEQ ID NO 246
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 246
tagggacgtt ccgcg                                                    15

<210> SEQ ID NO 247
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 247
tagggcgtcc taccg                                                    15

<210> SEQ ID NO 248
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 248
tagggctacg caccg                                                    15

<210> SEQ ID NO 249
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 249
taggtccgcg taacc                                                    15
```

```
<210> SEQ ID NO 250
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 250
taggtctatg cgcga                                                    15

<210> SEQ ID NO 251
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 251
taggttagcc gtacg                                                    15

<210> SEQ ID NO 252
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 252
tagtacgatc ccccg                                                    15

<210> SEQ ID NO 253
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 253
tagtacgcct cccga                                                    15

<210> SEQ ID NO 254
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 254
tagtacgcgt taggg                                                    15

<210> SEQ ID NO 255
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 255
tagtccgccc tacga                                                    15

<210> SEQ ID NO 256
<211> LENGTH: 15
<212> TYPE: DNA
<213> ORGANISM: Artificial Sequence
<220> FEATURE:
```

<223> OTHER INFORMATION: Synthetic oligonucleotide

<400> SEQUENCE: 256
tagtcgcgta acggg                                                    15

<210> SEQ ID NO 257
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 257
tatacgggcg tctag                                                    15

<210> SEQ ID NO 258
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 258
tatctatacg cggcc                                                    15

<210> SEQ ID NO 259
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 259
tattagcggg acccg                                                    15

<210> SEQ ID NO 260
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 260
tccgactagt agacg                                                    15

<210> SEQ ID NO 261
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 261
tccgcgctag gtcta                                                    15

<210> SEQ ID NO 262
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 262
tccgcggtta gttac                                                    15

```
<210> SEQ ID NO 263
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 263
tccgctagta cggggg                                                          15

<210> SEQ ID NO 264
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 264
tcgagtcgcc tagta                                                           15

<210> SEQ ID NO 265
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 265
tcgcccctag gcgta                                                           15

<210> SEQ ID NO 266
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 266
tcgcgactta ggccc                                                           15

<210> SEQ ID NO 267
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 267
tcgcgcatag accta                                                           15

<210> SEQ ID NO 268
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 268
tcgcggacct aagta                                                           15

<210> SEQ ID NO 269
<211> LENGTH: 15
<212> TYPE: DNA
<213> ORGANISM: Artificial Sequence
<220> FEATURE:
<223> OTHER INFORMATION: Synthetic oligonucleotide
```

<400> SEQUENCE: 269
tcgcgttagg taccc                                                   15

<210> SEQ ID NO 270
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 270
tcggcgtact aacgt                                                   15

<210> SEQ ID NO 271
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 271
tcgggaggcg tacta                                                   15

<210> SEQ ID NO 272
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 272
tcggtctacc cgtag                                                   15

<210> SEQ ID NO 273
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 273
tcgtaacgta ctagg                                                   15

<210> SEQ ID NO 274
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 274
tcgtagggcg gacta                                                   15

<210> SEQ ID NO 275
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 275
tctaacgcga cgtta                                                   15

<210> SEQ ID NO 276
<211> LENGTH: 15

```
<212> TYPE: DNA
<213> ORGANISM: Artificial Sequence
<220> FEATURE:
<223> OTHER INFORMATION: Synthetic oligonucleotide

<400> SEQUENCE: 276
tctaggcgta ccgac                                                      15

<210> SEQ ID NO 277
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 277
tctagtagcg cgacc                                                      15

<210> SEQ ID NO 278
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 278
tgcgacccgt cttac                                                      15

<210> SEQ ID NO 279
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 279
ttacgcgtag gtccg                                                      15

<210> SEQ ID NO 280
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 280
ttactagtcg cgcgt                                                      15

<210> SEQ ID NO 281
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 281
ttagacctat cgcgc                                                      15

<210> SEQ ID NO 282
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 282
```

```
ttaggccgtc ctacg                                                    15

<210> SEQ ID NO 283
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 283
cgcgacgtta a                                                        11

<210> SEQ ID NO 284
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 284
cgtcgctcga a                                                        11

<210> SEQ ID NO 285
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 285
tacgcgcgac a                                                        11

<210> SEQ ID NO 286
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 286
cgcgcataat a                                                        11

<210> SEQ ID NO 287
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 287
tcgcgcgaat a                                                        11

<210> SEQ ID NO 288
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 288
cgcgacgcat a                                                        11

<210> SEQ ID NO 289
<211> LENGTH: 11
<212> TYPE: DNA
<213> ORGANISM: Artificial Sequence
```

```
<220> FEATURE:
<223> OTHER INFORMATION: Synthetic oligonucleotide

<400> SEQUENCE: 289
tcgacgcgat a                                                           11

<210> SEQ ID NO 290
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 290
tcggtacgct a                                                           11

<210> SEQ ID NO 291
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 291
gcgcgacgtt a                                                           11

<210> SEQ ID NO 292
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 292
cgctcgacgt a                                                           11

<210> SEQ ID NO 293
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 293
cgacggacgt a                                                           11

<210> SEQ ID NO 294
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 294
tcgcgaccgt a                                                           11

<210> SEQ ID NO 295
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 295
gtccgagcgt a                                                           11
```

```
<210> SEQ ID NO 296
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 296
cgaatcgcgt a                                                              11

<210> SEQ ID NO 297
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 297
tgtcgcgcgt a                                                              11

<210> SEQ ID NO 298
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 298
cggtcgtacg a                                                              11

<210> SEQ ID NO 299
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 299
cgaatcgacg a                                                              11

<210> SEQ ID NO 300
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 300
atcgtcgacg a                                                              11

<210> SEQ ID NO 301
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 301
tagcgtaccg a                                                              11

<210> SEQ ID NO 302
<211> LENGTH: 11
<212> TYPE: DNA
<213> ORGANISM: Artificial Sequence
<220> FEATURE:
<223> OTHER INFORMATION: Synthetic oligonucleotide
```

```
<400> SEQUENCE: 302
gcgcgtaccg a                                                              11

<210> SEQ ID NO 303
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 303
cgcgtaatcg a                                                              11

<210> SEQ ID NO 304
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 304
ccgacgatcg a                                                              11

<210> SEQ ID NO 305
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 305
ctacgcgtcg a                                                              11

<210> SEQ ID NO 306
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 306
tatcgcgtcg a                                                              11

<210> SEQ ID NO 307
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 307
cgtatacgcg a                                                              11

<210> SEQ ID NO 308
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 308
cgattacgcg a                                                              11

<210> SEQ ID NO 309
```

```
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 309
tacggtcgcg a                                                    11

<210> SEQ ID NO 310
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 310
tattcgcgcg a                                                    11

<210> SEQ ID NO 311
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 311
cgatcgtgcg a                                                    11

<210> SEQ ID NO 312
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 312
cgattcggcg a                                                    11

<210> SEQ ID NO 313
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 313
cgtcgttcga c                                                    11

<210> SEQ ID NO 314
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 314
tacgctcgga c                                                    11

<210> SEQ ID NO 315
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 315
```

```
ccgtcgaacg c                                                      11

<210> SEQ ID NO 316
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 316
tcggtacgcg c                                                      11

<210> SEQ ID NO 317
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 317
taacgtcgcg c                                                      11

<210> SEQ ID NO 318
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 318
acgcgcgata t                                                      11

<210> SEQ ID NO 319
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 319
ccgcgcgata t                                                      11

<210> SEQ ID NO 320
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 320
tcgtcgacga t                                                      11

<210> SEQ ID NO 321
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 321
cgacgtaccg t                                                      11

<210> SEQ ID NO 322
<211> LENGTH: 11
<212> TYPE: DNA
```

```
<213> ORGANISM: Artificial Sequence
<220> FEATURE:
<223> OTHER INFORMATION: Synthetic oligonucleotide

<400> SEQUENCE: 322
ccgacgatcg t                                                           11

<210> SEQ ID NO 323
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 323
cgaacggtcg t                                                           11

<210> SEQ ID NO 324
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 324
atatcgcgcg t                                                           11

<210> SEQ ID NO 325
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 325
cgacgaacgg t                                                           11

<210> SEQ ID NO 326
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 326
cgcgtatcgg t                                                           11

<210> SEQ ID NO 327
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 327
tcgacgcgta g                                                           11

<210> SEQ ID NO 328
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 328
cgacgaacga g                                                           11
```

<210> SEQ ID NO 329
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 329
cgcgtaatac g                                                          11

<210> SEQ ID NO 330
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 330
cgcgctatac g                                                          11

<210> SEQ ID NO 331
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 331
tcgcgtatac g                                                          11

<210> SEQ ID NO 332
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 332
cgaccgatac g                                                          11

<210> SEQ ID NO 333
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 333
gtcgaacgac g                                                          11

<210> SEQ ID NO 334
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 334
ttcgagcgac g                                                          11

<210> SEQ ID NO 335
<211> LENGTH: 11
<212> TYPE: DNA
<213> ORGANISM: Artificial Sequence
<220> FEATURE:

```
<223> OTHER INFORMATION: Synthetic oligonucleotide

<400> SEQUENCE: 335
tcgtacgacc g                                                        11

<210> SEQ ID NO 336
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 336
tcgcgtaatc g                                                        11

<210> SEQ ID NO 337
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 337
tcgccgaatc g                                                        11

<210> SEQ ID NO 338
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 338
tcgcacgatc g                                                        11

<210> SEQ ID NO 339
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 339
tcgtcgattc g                                                        11

<210> SEQ ID NO 340
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 340
tacgcgattc g                                                        11

<210> SEQ ID NO 341
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 341
acgaccgttc g                                                        11
```

```
<210> SEQ ID NO 342
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 342
ccgatacgtc g                                                              11

<210> SEQ ID NO 343
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 343
ccgttacgtc g                                                              11

<210> SEQ ID NO 344
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 344
acggtacgtc g                                                              11

<210> SEQ ID NO 345
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 345
tacgtccgtc g                                                              11

<210> SEQ ID NO 346
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 346
accgttcgtc g                                                              11

<210> SEQ ID NO 347
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 347
ctcgttcgtc g                                                              11

<210> SEQ ID NO 348
<211> LENGTH: 11
<212> TYPE: DNA
<213> ORGANISM: Artificial Sequence
<220> FEATURE:
<223> OTHER INFORMATION: Synthetic oligonucleotide
```

```
<400> SEQUENCE: 348
cgtatcggtc g                                                          11

<210> SEQ ID NO 349
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 349
tacgtcgagc g                                                          11

<210> SEQ ID NO 350
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 350
cgcgtaacgc g                                                          11

<210> SEQ ID NO 351
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 351
ccgaatacgc g                                                          11

<210> SEQ ID NO 352
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 352
accgatacgc g                                                          11

<210> SEQ ID NO 353
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 353
cgtattacgc g                                                          11

<210> SEQ ID NO 354
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 354
tcgattacgc g                                                          11

<210> SEQ ID NO 355
<211> LENGTH: 11
```

```
<212> TYPE: DNA
<213> ORGANISM: Artificial Sequence
<220> FEATURE:
<223> OTHER INFORMATION: Synthetic oligonucleotide

<400> SEQUENCE: 355
cgcgttacgc g                                                              11

<210> SEQ ID NO 356
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 356
ttaacgtcgc g                                                              11

<210> SEQ ID NO 357
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 357
tatgcgtcgc g                                                              11

<210> SEQ ID NO 358
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 358
cgtatagcgc g                                                              11

<210> SEQ ID NO 359
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 359
catatcgcgc g                                                              11

<210> SEQ ID NO 360
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 360
tattatgcgc g                                                              11

<210> SEQ ID NO 361
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 361
```
cgcgcgatat g                                                                11

<210> SEQ ID NO 362
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 362
cgacgtaacg g                                                                11

<210> SEQ ID NO 363
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 363
gcgttcgacg g                                                                11

<210> SEQ ID NO 364
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 364
cgacgtatcg g                                                                11

<210> SEQ ID NO 365
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 365
cgcgtattcg g                                                                11

<210> SEQ ID NO 366
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 366
acgatcgtcg g                                                                11

<210> SEQ ID NO 367
<211> LENGTH: 11
<212> TYPE: DNA
<213> ORGANISM: Artificial Sequence
<220> FEATURE:
<223> OTHER INFORMATION: Synthetic oligonucleotide

<400> SEQUENCE: 367
tcgatcgtcg g                                                                11

<210> SEQ ID NO 368
<211> LENGTH: 11
<212> TYPE: DNA
<213> ORGANISM: Artificial Sequence

```
<220> FEATURE:
<223> OTHER INFORMATION: Synthetic oligonucleotide

<400> SEQUENCE: 368
atatcgcgcg g                                                          11

<210> SEQ ID NO 369
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 369
cgacgtatcg gaccgttcgt cgccgatacg tcgcgacgaa cggttacgct cggacgtccg     60
agcgtacgct cgacgta                                                    77

<210> SEQ ID NO 370
<211> LENGTH: 120
<212> TYPE: DNA
<213> ORGANISM: Artificial Sequence
<220> FEATURE:
<223> OTHER INFORMATION: Synthetic oligonucleotide

<400> SEQUENCE: 370
tactaggcga ctcgacggtc ttacgcgtta cgtccgacta tagagcttag attagcgacg     60
ttagacctat cgcgccttag attagcgacg ctagcgtacg ctacggtcct aacgcgctat    120

<210> SEQ ID NO 371
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 371
taggcgactc gacggtctta cgcgttacgt                                      30

<210> SEQ ID NO 372
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 372
gcgcgttagg accgtagcgt acgctagcgt                                      30

<210> SEQ ID NO 373
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 373
tactaggcga ctcgacggtc                                                 20

<210> SEQ ID NO 374
<211> LENGTH: 25
<212> TYPE: DNA
<213> ORGANISM: Artificial Sequence
<220> FEATURE:
<223> OTHER INFORMATION: Synthetic oligonucleotide
```

-continued

```
<400> SEQUENCE: 374
tcgctaatct aaggcgcgat aggtc                                              25

<210> SEQ ID NO 375
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 375
tactaggcga ctcgacggtc                                                    20

<210> SEQ ID NO 376
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 376
cgtcgctaat ctaaggcgcg a                                                  21

<210> SEQ ID NO 377
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 377
taggaccgta gcgtacgcta gcgtcgctaa                                         30
```

REFERENCE MARKERS FOR BIOLOGICAL SAMPLES

REFERENCE MARKERS FOR BIOLOGICAL SAMPLES

This application claims priority to and is a continuation-in-part of pending U.S. patent application Ser. No. 12/941,860, filed Nov. 8, 2010. 12/941,860 is a Division of and claims priority to U.S. patent application Ser. No. 11/024,293, filed Dec. 23, 2004, now abandoned and U.S. Provisional Patent Application 60/532,673, filed Dec. 23, 2003. The complete contents of each of these are hereby incorporated by reference.

FIELD OF THE INVENTION

The invention generally relates to reference markers (RMs) for biological samples, particularly biological samples that contain or are likely to contain nucleic acids such as DNA. The RMs are oligonucleotides comprising DNA oligomers derived using a system that identifies all sequences of specified lengths that do not exist in (i.e. are absent from) the genome of one or more organisms of interest. The RMs are added to the biological sample in order to "tag" and subsequently identify the sample as authentic, e.g. in forensic, medical, legal or other applications.

BACKGROUND TO THE INVENTION

DNA profiles are routinely used in criminal, paternity, and human identification procedures. The US military requires samples from every soldier, and every state in America requires DNA samples from convicted offenders of qualifying crimes. In addition to these targeted groups, many people are asked to give samples as victims or suspects of crimes.

Reference samples are those given by (or obtained from) known individuals who are part of a forensic, medical, legal or other identification investigation. These samples may be obtained from living or deceased individuals, or from items presumed to be derived from those individuals. A typical example is a blood or buccal sample obtained from a suspect in a criminal investigation.

Once reference samples are obtained, the integrity of the subsequent investigation and analysis depends on the integrity of the reference samples. An investigation can be completely compromised by the cross contamination of reference sample and evidentiary material. There is presently no standard marker added to blood, buccal or other biological reference samples which prevents their accidental or malicious deposition at crime scenes, or in or on evidence samples. In addition, it is not uncommon for the same individuals to handle reference and evidentiary samples. Should cross-contamination occur there is no reliable mechanism of demonstrating that it has happened.

Biological samples are now taken as a standard part of numerous forensic, medical, legal and identification procedures. Several states have enacted legislation defining the length of time that state agencies and forensic laboratories can hold reference samples, but others can hold these samples indefinitely. This has led to a concern on the part of those who provide the samples that errors or malicious intent could lead to their samples being mishandled, thus implicating them in criminal activity. While the DNA in a biological sample serves as an individuating identification of the donor, it says nothing of the manner in which it was obtained. The vast majority of DNA samples are taken as reference samples (known identity), and these must remain separate from evidentiary samples (unknown samples). While several patents address the labeling of samples with chemical markers, none of them satisfy the issues inherent in forensic DNA analysis.

U.S. Patent Application No. 20040072199 discloses a method for marking samples containing DNA by means of oligonucleotides. This invention does not address forensic applications, and the oligomers disclosed are artificial microsatellites and single nucleotide polymorphisms, designed without reference to avoiding sequences that might be encountered in typical forensic samples.

WO 96/17954 discloses a method for chemical identification of an object, wherein according to the invention at least two chemical markers are used. One marker shows that the container itself has been marked, while the other marker is in principle the real identification. However, such markings are not based on DNA sequences that would be readily detectable using the methodologies common in forensic, paternity and human identification laboratories.

U.S. Pat. No. 5,776,737 discloses a method for the identification of samples, wherein oligonucleotides are added to the sample obtained, which will be sequenced together with the sample after a subsequent amplification step. The oligonucleotides consist of a primer binding site and an identification region consisting of an alternating sequence of nucleotides (MN)x and (MNN)x, respectively, wherein N is the nucleotide of the primer binding site. The sample can be identified by sequencing the identification region. However, this method requires sequencing, and does not address the question of oligomer design in terms of avoiding sequences commonly encountered in forensic samples.

International Patent No. 20030177095 describes a system of authentication and/or tracking for identifying, tracking, authenticating and/or otherwise checking the legitimacy of one or more items which include a coded identity tag or mark, the system comprising identification means for reading said coded identity tag or mark and identifying said one or more items, storage means for storing information relating to the location, whether actual or intended, origin and/or ownership of said one or more items, and means for displaying or otherwise providing or verifying said information relating to an item when its identity tag or mark has been read. However, this system does not cover the specific application of identifying biological reference samples in order to distinguish them from evidentiary samples. It also does not embody a tag that will be identified using the standard techniques in use by forensic, medical, legal and identification laboratories namely Polymerase Chain Reaction and mitochondrial DNA sequencing. Rather it applies to a system which uses tags "preferably in the form of a coded fibre or filament" (claim 3); which can be read by a "bar code reader or scanner" (claim 4). While the claim mentions DNA in its summary (2) as a possible "tag" it does not describe any specific applications or methods using DNA as a tag.

Several patents describe forensic primer sets which are used to amplify human short tandem repeat (STR) regions of the genome. For example, U.S. Pat. No. 6,251,592, for example, discloses (Short Tandem Repeat) STR markers for DNA fingerprinting. This patent is a refinement on the standard technology of DNA fingerprinting for human identification using STR markers.

The prior art has thus far failed to provide a system whereby nucleic acid samples such as forensic reference samples can be marked with amplifiable DNA tags to distinguish the samples from other unmarked samples, thereby establishing their authenticity in a manner compatible with common identification methods such as forensic profiling.

SUMMARY OF THE INVENTION

The invention provides reference markers (RMs), the nucleic acid sequences of which include one or more of the smallest sequences which are absent from a genome or genomes of interest. The absent sequences are identified by analyzing the nucleotide sequence(s) of the one or more genomes of interest using an algorithm that detects sequences that do not occur within the genomic sequence(s). The absent sequences are generally between 11 and 20 nucleotides in length (e.g. 15 nucleotides), but may be longer, and the oligomeric RMs comprise at least one, and usually multiple copies, of one or more absent sequences. The oligomeric RMs are added to biological samples, especially biological samples which are known to contain, or are suspected of containing, genomic DNA or fragments thereof, in order to "tag" or label the samples. As a result, an analysis of the DNA present in a "tagged" sample (e.g. by PCR, sequencing or other means) will reveal the presence of both the RMs and any DNA that was present in the sample. Positive detection of the RM sequences in a sample confirms the history of the sample, and establishes that the sample is authentic. Conversely, if the RMs are not detected in a sample that is purportedly authentic, then the sample may be considered suspect or spurious, either as a result of error, malicious intent or for some other reason. Furthermore, if the RMs are detected e.g. in a forensic sample, which should not contain the RM, then the sample may be considered suspect or spurious, either as a result of error, malicious intent or for some other reason. The RMs are used in conjunction with many applications that involve DNA testing or profiling, for example, in forensic, paternity, archeological and other investigations. In one embodiment, the RMs are used to label and hence distinguish reference from evidentiary samples in forensic investigations. The detection of the RM in evidentiary samples, reagents, or swabs from instruments or work surfaces would indicate contamination of those items. Thus, the RM also serves as a quality control marker for forensic and other DNA laboratories. The RMs also serve as positive amplification control showing that reagents are working properly, and indicating the level of any PCR or profiling inhibitors. Further, if two different sizes of RMs are included in a sample, e.g. in a sample that is stored, detection of differential amounts of the two (e.g. a greater level of loss of a longer RM compared to a level of loss of a shorter RM) may be indicative of the extent of degradation of the sample. In addition, the oligomers or RMs of the invention can serve as virtual or computerized sensing tools for sequences, e.g. for the fidelity of copied data sets, to test for corruption of nucleic acid codes in databases, etc. since detection of the oligomers or RMs of the invention in a data set should not occur. If the oligomer or RM sequences are detected, this is in indication that the data set has been incorrectly copied or corrupted, or is otherwise vitiated. The detection of RM sequences can also detect the introduction of suspected artificial, mutated, or extraterrestrial biological sequences.

The present invention also provides a composition which includes a biological sample that contains at least one oligonucleotide reference marker (RM) as described herein. The reference oligonucleotide sequence does not overlap with a nucleotide sequence found in the genome of a living animal or organism, for example the human genome. In one embodiment the reference oligonucleotide can contain at least one oligomer comprising at least about 11 or 12 consecutive or contiguous nucleotides, and usually at least one oligomer that includes at least about 15 nucleotides, which are not present in the genome of a living animal or organism. In other embodiments, the reference oligonucleotide may contain multiple copies of the unique oligomers described herein, e.g. at least 8 copies of 15 nt oligomers, i.e. at total of 120 or more nucleotides per RM. This invention also provides methods and kits to produce such reference markers for use in forensic, medical, legal, and other applications. The present invention may be utilized in conjunction with many prior art DNA analysis techniques, such as those described in the background section, to insure the identity and authenticity of the samples that are analyzed.

It is therefore an object of this invention to provide reference markers for use in biological samples that do not overlap with the information contained in the biological sample. It is another object of the present invention to provide methods to identify reference markers for use in biological samples that do not overlap with the information contained in the biological sample. It is further object of the present invention to provide kits for use in forensic, medical or other applications that include reference markers that do not overlap with the information contained in the biological sample.

In one embodiment, a method to produce standard reference markers (RMs) to mark and identify biological reference samples. In a second embodiment, a method is provided to add or incorporate the RMs in materials used to collect, transfer and store biological reference samples. In a third embodiment, a method to identify the RMs using techniques that are employed by laboratories involved in identification, processing and analysis of forensic, medical and legal biological reference samples.

In one aspect of the invention, nucleotide sequences are provided that are not found in living organisms, such as in the human genome, especially the smallest of those sequences. A method is provided to generate such sequences by searching the genomes of known organisms. The method includes an iterative search of selected data sets looking for progressively larger sequences not found in the data. Thus, the program looks first for the appearance of each two base combination, then each 3 base combination, etc. The number of possible sequences is represented by the formula $4^n$, where n is the length of the sequence. For example, for an eleven base sequence, the possible number of oligomers is $4^{11}$, or 4,194,304. For a 15 base sequence, there are 1,073,741,824 possible combinations. When the program determines that a sequence is not present in the selected data set, it records it as a nullomer.

In one embodiment, a method is provided to distinguish reference samples from those obtained as unknown, questioned or evidentiary samples. This can be achieved because the RM added to the biological reference sample can be detected by PCR, or DNA sequencing.

In one particular embodiment, a Reference Marker (RM) nucleic acid molecule of known sequence and size can be added to reference samples as part of the collection process. The molecules can be included in the containers used to collect, transport and store these samples, such as containers for: buccal swabs, blood, other tissue, and hair samples. The RM can provide a method of distinguishing reference samples from evidentiary, questioned, and unknown samples. RMs can also provide an indicator for tampering with, misidentification of and misinterpretation of reference samples.

The sequence of the RMs can be formulated so as not to interfere with the commonly used kits for STR analysis. Furthermore, when amplified with primers, the RMs can produce amplicons outside of the range of known human alleles produced by the STR primers in common use by legal, criminal, military, and other human identification laboratories. The RMs also can be formulated so as not to interfere with mitochondrial sequencing. RM primers can be designed in a manner known to those skilled in the art designing STR primers, wherein the primers do not amplify unintended human sequences, or produce amplicons of the reference marker size when combined with materials commonly found in crime scenes.

The RMs can be human "nullomers". Human nullomers are small sequences which are not present in the human genome. These have been determined by an iterative search algorithm which queries sequences (downloaded to a server) for the complete set of 11, and 12 base sequence possibilities. Based on this analysis 11 and 12 nucleotide base sequences not found in the published human genome sequences can be identified. These sequences that are not found in the genome, we have given the name nullomers. These nullomers can also be searched against the entire set of known sequences in the biosphere, and those sequences that are not found in any species we have given the name "primes." From the set of nullomers and primes, RMs and their associated primers can be designed.

The RMs can be made of DNA molecules that are either single or double stranded, synthesized oligomers or engineered fragments isolated from vectors. Other nucleotides, nucleotide analogs and organic molecules can be incorporated into the RMs so as compliment STR analysis and sequencing systems.

DETAILED DESCRIPTION OF THE DRAWINGS

FIGS. 1A and B. Nullomer Tag does not interfere with Quantifier DUO™ DNA quantification. A, this DNA qPCR quantification standard curve uses control DNA supplied with the Quantifier DUO™ kit from Applied Biosystems. The DNA standard was diluted according to manufacturer's instructions, and the real-time PCR performed according to the manufacture's protocol. Number of cycles to reach the quantification threshold (Cq) is shown, for DNA with (○) and without (□) $1.9 \times 10^3$ copies of nullomer barcode. B, HV2 region of mitochondrial DNA from male (left) and female (right) amplified in the presence and absence of the nullomer barcode. Mitochondrial PCR product was visualized on a 3% agarose gel. HV2 product amplified properly with nullomer barcode (with and without nullomer primers added to the HV2 PCR reaction).

Figure 2:
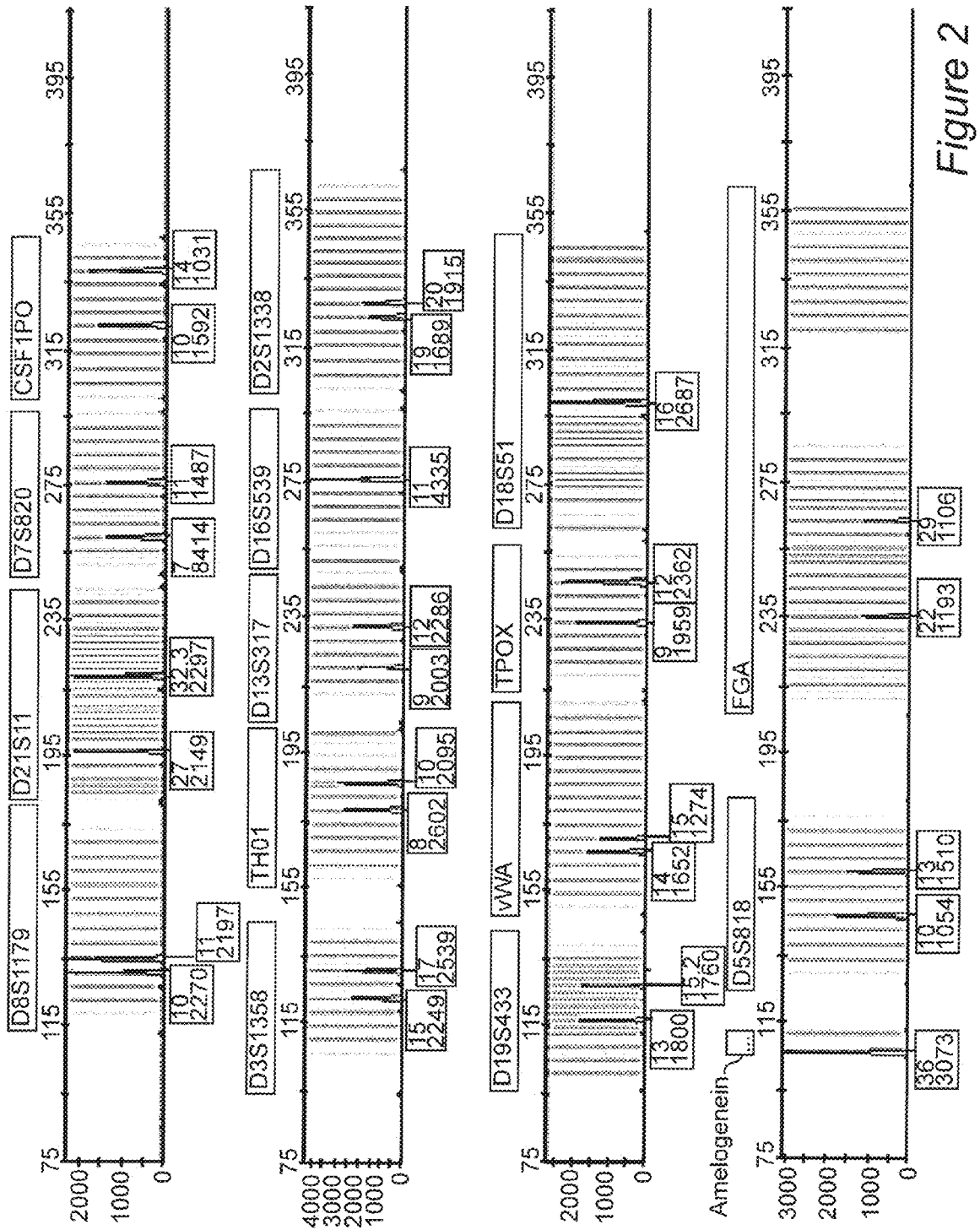

FIG. 2. STR profile of female genomic DNA amplified with Identifiler™ kit in absence of barcode. Size of each amplified product is given in bp, the locus is indicated by labels above the peaks. Labels below peaks indicate the number of repeats (allele) and the relative fluorescence units (RFU) value. The y-axis is in RFUs, and is scaled according to maximum peak height.

Figure 3:
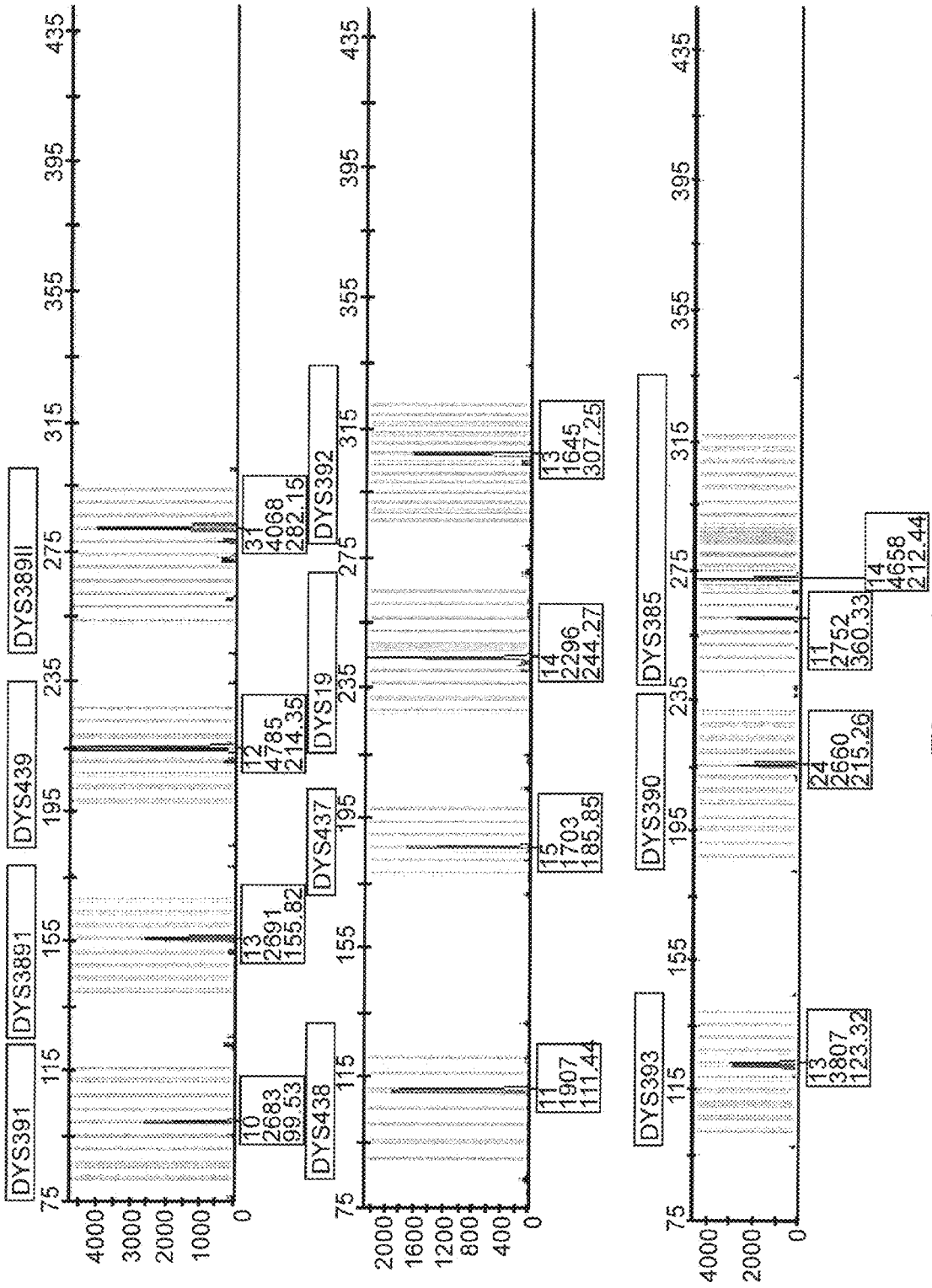

FIG. 3. Male DNA amplified with Yplex™ kit in presence of nullomer barcode. No nullomer barcode present in this reaction. The y-axis scale is in relative fluorescence units (RFU). The label for each peak indicates the number of repeats (allele) and the RFU value. Locus DYS385 shows repetition. In Yplex kit nullomer barcode appears as an off ladder peak in the first locus (DYS391).

Figure 4:
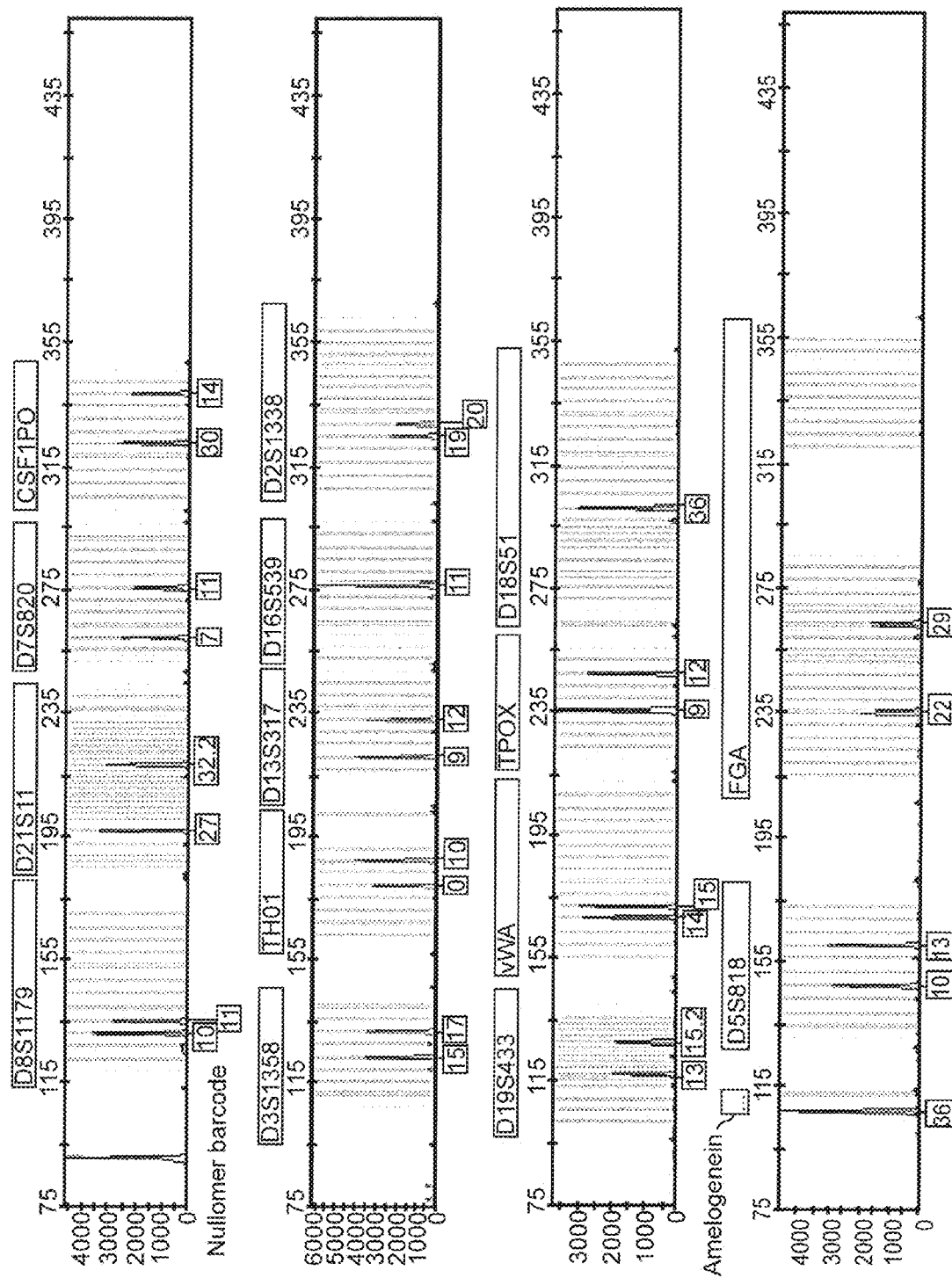

FIG. 4. DNA extracted from nullomer barcode-impregnated FTA paper, amplified with the Identifiler™ kit. DNA was extracted from nullomer barcode-impregnated FTA paper. Five punches of FTA paper were used for extraction. The y-axis indicates the corresponding RFU value for each peak.

Figure 5:
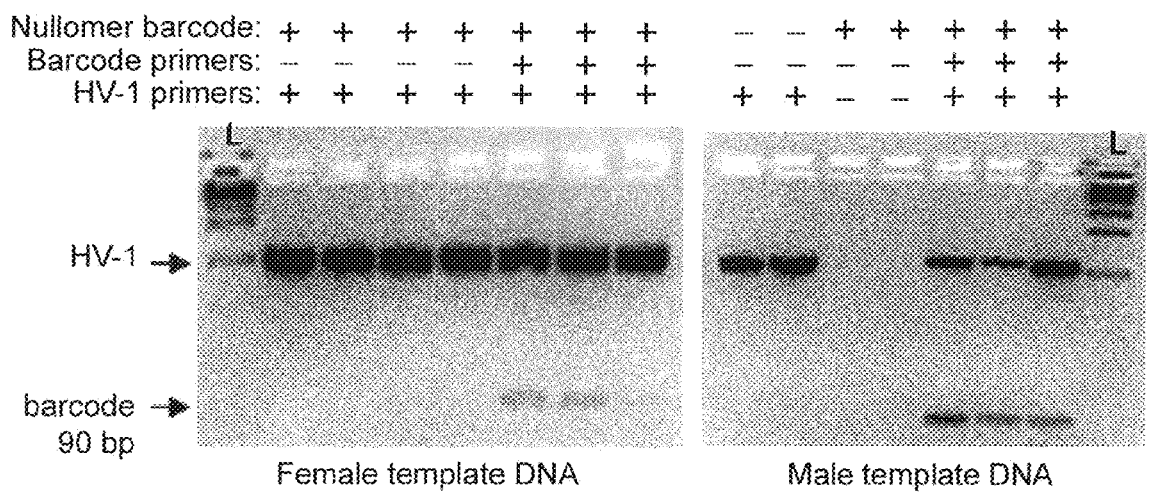

FIG. 5. Human mitochondrial DNA amplified with nullomer barcode. Mitochondrial PCR product was visualized on 3% agarose gel. Presence or absence of target (HV-1) and barcode amplification products are indicated for the different primer combinations used in each reaction (bands at about 500 and 100 bp, respectively).

Figure 6:
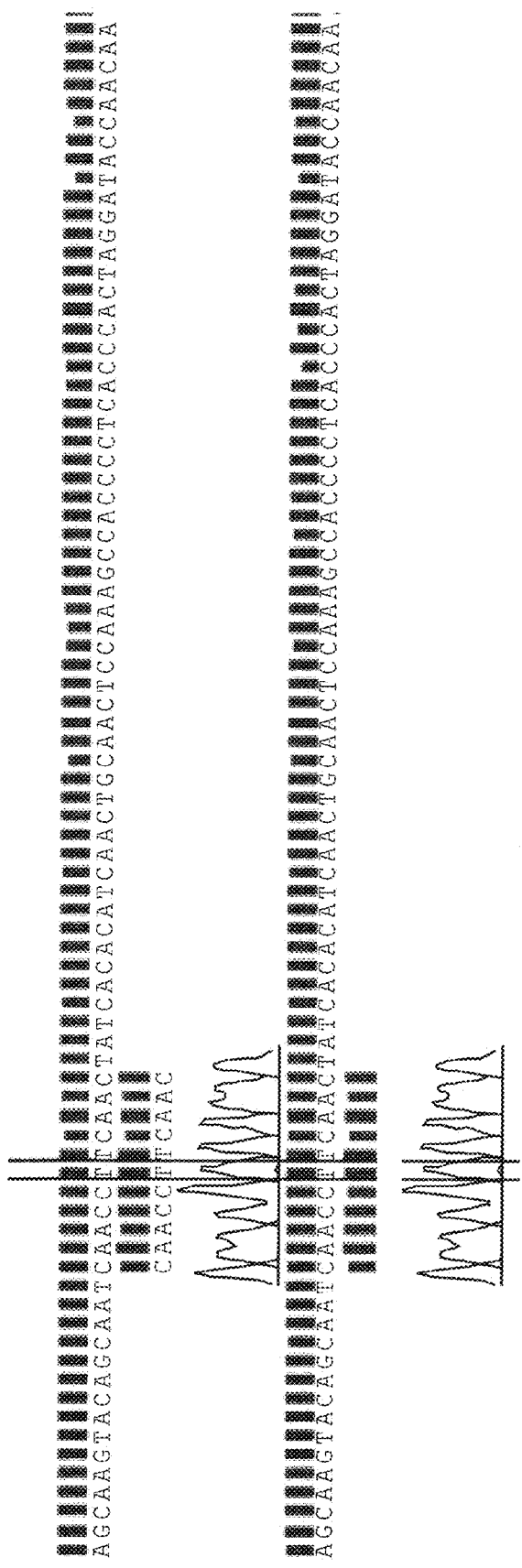

FIG. 6. Sequence of HV-1 region from female volunteer, from DNA sample tagged with nullomer barcode. 1,900 copies Nullomer barcode added to initial PCR reaction, and another 1,900 copies added to sequencing reactions (Big Dye 3.1 kit, ABI). No nullomer primers were added. The sequences obtained are identical; with nearly identical QV scores for each read (blue bars). Electropherogram detail is shown around the position 16223, where a T is common in the individual's mitochondrial haplogroup (in the Cambridge reference sequence, 16223 is a C).

FIGS. 7A and B. Contamination of evidence with amplified DNA is detected with nullomer barcode, even when diluted 1,000,000 fold. A (and insert), DNA from amplified STR profile (amplified with nullomer barcode) was diluted 100,000 times in water, and then 1 ul of the dilution was applied to a newly purchased knife. This knife was swabbed, and amplified according to the STR kit manufacture's instructions (with the addition of nullomer primers). STR profile from contaminated knife shows both the contaminating profile, and the nullomer barcode peak. B, Electropherogram: original PCR product was diluted 1:1,000,000 in water, and 1 ul of the diluted product was added to a newly purchased knife. The knife was swabbed and processed as above. The nullomer barcode amplicon is prominent, although no alleles from the amplified human profile are detected.

DETAILED DESCRIPTION OF THE INVENTION

The current invention solves a long felt need to ensure the validity and authenticity of samples submitted in forensic, paternity, and other inquiries which utilize DNA analysis in order to establish the identity of a DNA donor. The current invention offers several distinct advantages over standard prior art methods, including but not limited to: the design of reliable, non-dilutable makers suitable for forensic applications, compatibility with standard DNA identification procedures, and a built-in system for laboratory validation concerning the separation of, for example, reference and evidentiary samples. In addition, the methodology is extremely flexible in that a plethora of unique and varied sequences can be designed and tailored to the needs of a particular application.

I: Definitions

The term "RMs" refers to reference markers which are isolated and purified artificial (synthetic) oligonucleotides which comprise at least one copy, and usually a plurality of copies, of a sequence that does not occur (is absent from) one or more genomes of interest. In one embodiment, RMs are added to biological samples (e.g. reference samples) collected from known individuals or sources during the course of forensic, paternity, and other human identification procedures in order to tag or label the samples.

The term "nullomers" refers to oligonucleotide sequences that are not present in the published genome sequences representing a single species.

The term "primes" refers to oligonucleotide sequences that are not present in any reported, published sequence for any species, i.e. these sequences are the smallest (shortest, fewest contiguous nucleotides) that are not present in any sequence of any publicly available biological databases of natural species.

The term "PCR" refers to polymerase chain reaction used to amplify minute amounts of DNA. PCR is a common molecular biology technique in which cycles of denaturation, primer annealing, and primer extension with DNA polymerase, are used to multiply the number of copies of a specific sequence.

The term "amplicons" refers to the amplified products of PCR.

The term "short tandem repeat" (STR) refers to sequences between 2 and 7 nucleotides in length which are tandemly reiterated within the human organism. The STR repeats are usually reiterated between 3 and 50 times.

The term "STR profiling" refers to a length based PCR technique, which is used to identify individuals.

The term "single nucleotide polymorphism" SNP, refers to alternative nucleotide base sequences which differ by a single base. SNPs form the basis of many forms of analysis common in the art.

As used herein, the term "animal" is meant to include any non-human animal, particularly any non-human mammal, including but not limited to pigs, sheep, goats, cattle (bovine), deer, mules, horses, monkeys, dogs, cats, rats, mice, birds, chickens, C. elegans, D. melanogaster, reptiles, fish, and insects, including species which are or are thought to be extinct.

II: Determination of Nullomers and Primes

Sequences publicly available on the internet at sites such as the NCBI website can be downloaded and searched using nucleotide sequences of a given length or lengths, for example, the complete set of 11, 12 or 15 base oligomer combinations. For any species, the full set of oligomers that are not found in that species can be termed nullomers. In one embodiment of the invention, nullomers form the basis of the RM sequences to be used to mark reference samples.

In one embodiment, the nullomers described herein can be used as reference markers. In one embodiment, the nullomers can be at least 11, 12 or 15 nucleotides in length. From these 11 or more nucleotide nullomers, oligonucleotide reference markers of any size can be generated by combining, in a single RM oligonucleotide, at least one copy of one nullomer, or multiple copies of one nullomer, or one copy each of several nullomers, or one or multiple copies of each of several nullomers, or combinations of these. In one embodiment, the reference markers can be at least about 15 bp, 20 bp, 25 bp, 50 bp, 100 bp, 500 bp, 1 kbp, 2 kbp, 4 kbp, 5 kbp, 10 kbp, 15 kbp, 20 kbp, or 50 kbp or more nucleotides in length. In another embodiment, the reference markers can be at least about 70%, 75%, 80%, 85%, 90%, 95%, 95.5%, 96%, 96.5%, 97%, 97.5%, 98%, 98.5%, 99% or 99.5% homologous to the nullomers.

For example, for human identification RMs, the set of RMs can be derived from the set of 11, 12 or 15 base nullomers determined for the human species. The set of 11 base nullomers derived from two published sequences of the human genome are shown in Table 1. The sequences in bold represent 11 base sequences that are not found in any publicly listed sequence in the NCBI database as determined by BLAST searching on Oct. 12, 2004. These sequences that have not been reported in any species are called "primes". In one embodiment, the primes are of great value to molecular biology in that they can form the basis of an artificial DNA code, representing sequences that are not found in nature. These sequences are useful as tags which, when detected, indicate the presence of unexpected and possibly synthetic (or at least previously unknown) DNA. This capability could be useful, for example, in investigations of: fossilized remains: samples from locations that are rarely or never-before accessed (e.g. planets other than earth, environments considered to be inhospitable to life such as hot springs, the deep ocean, extreme cold, etc. In addition, the properties and novel consequences of these sequences at the DNA, RNA and protein levels in engineered systems can be exploited as novel features of engineered organisms.

Table 2 below lists 282 15 base human nullomers that are also not found in the known genomes of any other species, i.e. they are primes. These primes were identified as described herein. Briefly, the entire set of publicly available NCBI DNA databases were downloaded, and an iterative search was made of all possible combinations of nucleotides from length 2-17. Absent sequences were first noted at length 15. Counts of all length 15-17 sequences were recorded. The 0 count primes were used to construct the tags described and depicted in the accompanying illustrations.

In a further embodiment of the invention, the list of nullomers and primes can be refined by updated searches of sequence databanks as they are developed. In another embodiment, reference markers can contain at least one nullomer or prime selected from the sequences listed in Tables 1, 2 and 3 below, or their DNA compliments, and/or RNA equivalents. In a further embodiment, the nullomers can be at least 13 bp, 20 bp, 25 bp, 50 bp, 100 bp, 500 bp, 1 kbp, 2 kbp, 4 kbp, 5 kbp, 10 kbp, 15 kbp, 20 kbp, or 50 kbp nucleotides in length, which are identified as described herein.

TABLE 1

"Nullomers" not found in the human genome as of 2004.

| 11 base Nullomers (Human) | Sequence | SEQ ID NO: |
|---|---|---|
| 1 | cgcgacgttaa | 283 |
| 2 | cgtcgctcgaa | 284 |
| 3 | tacgcgcgaca | 285 |
| 4 | cgcgcataata | 286 |
| 5 | tcgcgcgaata | 287 |
| 6 | cgcgacgcata | 288 |
| 7 | tcgacgcgata | 289 |
| 8 | tcggtacgcta | 290 |
| 9 | gcgcgacgtta | 291 |
| 10 | cgctcgacgta | 292 |
| 11 | cgacggacgta | 293 |
| 12 | tcgcgaccgta | 294 |
| 13 | gtccgagcgta | 295 |
| 14 | cgaatcgcgta | 296 |
| 15 | tgtcgcgcgta | 297 |
| 16 | cggtcgtacga | 298 |
| 17 | cgaatcgacga | 299 |
| 18 | atcgtcgacga | 300 |
| 19 | tagcgtaccga | 301 |
| 20 | gcgcgtaccga | 302 |
| 21 | cgcgtaatcga | 303 |
| 22 | ccgacgatcga | 304 |

TABLE 1 -continued

"Nullomers" not found in the human genome as of 2004.

| 11 base Nullomers (Human) | Sequence | SEQ ID NO: |
|---|---|---|
| 23 | ctacgcgtcga | 305 |
| 24 | tatcgcgtcga | 306 |
| 25 | cgtatacgcga | 307 |
| 26 | cgattacgcga | 308 |
| 27 | tacggtcgcga | 309 |
| 28 | tattcgcgcga | 310 |
| 29 | cgatcgtgcga | 311 |
| 30 | cgattcggcga | 312 |
| 31 | cgtcgttcgac | 313 |
| 32 | tacgctcggac | 314 |
| 33 | ccgtcgaacgc | 315 |
| 34 | tcggtacgcgc | 316 |
| 35 | taacgtcgcgc | 317 |
| 36 | acgcgcgatat | 318 |
| 37 | ccgcgcgatat | 319 |
| 38 | tcgtcgacgat | 320 |
| 39 | cgacgtaccgt | 321 |
| 40 | ccgacgatcgt | 322 |
| 41 | cgaacggtcgt | 323 |
| 42 | atatcgcgcgt | 324 |
| 43 | cgacgaacggt | 325 |
| 44 | cgcgtatcggt | 326 |
| 45 | tcgacgcgtag | 327 |
| 46 | cgacgaacgag | 328 |
| 47 | cgcgtaatacg | 329 |
| 48 | cgcgctatacg | 330 |
| 49 | tcgcgtatacg | 331 |
| 50 | cgaccgatacg | 332 |
| 51 | gtcgaacgacg | 333 |
| 52 | ttcgagcgacg | 334 |
| 53 | tcgtacgaccg | 335 |
| 54 | tcgcgtaatcg | 336 |
| 55 | tcgccgaatcg | 337 |
| 56 | tcgcacgatcg | 338 |
| 57 | tcgtcgattcg | 339 |
| 58 | tacgcgattcg | 340 |

TABLE 1 -continued

"Nullomers" not found in the human genome as of 2004.

| 11 base Nullomers (Human) | Sequence | SEQ ID NO: |
|---|---|---|
| 59 | acgaccgttcg | 341 |
| 60 | ccgatacgtcg | 342 |
| 61 | ccgttacgtcg | 343 |
| 62 | acggtacgtcg | 344 |
| 63 | tacgtccgtcg | 345 |
| 64 | accgttcgtcg | 346 |
| 65 | ctcgttcgtcg | 347 |
| 66 | cgtatcggtcg | 348 |
| 67 | tacgtcgagcg | 349 |
| 68 | cgcgtaacgcg | 350 |
| 69 | ccgaatacgcg | 351 |
| 70 | accgatacgcg | 352 |
| 71 | cgtattacgcg | 353 |
| 72 | tcgattacgcg | 354 |
| 73 | cgcgttacgcg | 355 |
| 74 | ttaacgtcgcg | 356 |
| 75 | tatgcgtcgcg | 357 |
| 76 | cgtatagcgcg | 358 |
| 77 | catatcgcgcg | 359 |
| 78 | tattatgcgcg | 360 |
| 79 | cgcgcgatatg | 361 |
| 80 | cgacgtaacgg | 362 |
| 81 | gcgttcgacgg | 363 |
| 82 | cgacgtatcgg | 364 |
| 83 | cgcgtattcgg | 365 |
| 84 | acgatcgtcgg | 366 |
| 85 | tcgatcgtcgg | 367 |
| 86 | atatcgcgcgg | 368 |

TABLE 2

15 base primes as of 2007
(note: the nucleotide compliments of these sequences are also primes). Shading indicates sequences used in the example 2 below.

| #   | Sequence        | #   | Sequence        | #   | Sequence        |
|-----|-----------------|-----|-----------------|-----|-----------------|
| 1   | AACTTCGCTAGCGGG | 101 | CGGTCTTACGCGTTA | 201 | GTTAGCTACGCCCGG |
| 2   | ACCCTAAGGCGCGTA | 102 | CGGTGCGTAGCCCTA | 202 | GTTCGCGTACTAGCG |
| 3   | ACCGGGCTAGTCGTA | 103 | CGGTTAGTACGACCG | 203 | GTTGATAGGACGCGC |
| 4   | ACCTAGTTCGCGCTA | 104 | CGTAAGACCGGACCC | 204 | TAACGCGGTCTAGAC |
| 5   | ACGATAGTCTAACGC | 105 | CGTACGCGGACTAGC | 205 | TAACGCGTAAGACCG |
| 6   | ACGCGACCGCTAAGT | 106 | CGTACGGCTAACCTA | 206 | TAACGTAGCGCGGAC |
| 7   | ACGCGCGACTAGTAA | 107 | CGTAGCGTACGCTAG | 207 | TAACGTCGCGTTAGA |
| 8   | ACGGACTAGCGCGCT | 108 | CGTAGGACCGTTAAG | 208 | TAACTAGCGTCCGCG |
| 9   | ACGGTTAGGCCCGTA | 109 | CGTAGGACGGCCTAA | 209 | TAAGCCGTAGTACGG |
| 10  | ACGTAGGGTTACGCG | 110 | CGTAGGATAGTCCCG | 210 | TAAGCTACGGGCGTA |
| 11  | ACGTTAGTACGCCGA | 111 | CGTAGGGCGTACTTA | 211 | TAAGTACGCCCTACG |
| 12  | ACTAACGTCTCGCGC | 112 | CGTAGTCCCCGCTAG | 212 | TAAGTCCGCTACGCG |
| 13  | ACTACGCGTAGGGTC | 113 | CGTCCGACTATAGAG | 213 | TACCCGGACGACTAG |
| 14  | ACTAGCGGTCCGACG | 114 | CGTCGCTAATCTAAG | 214 | TACCCGTCTAAGCGC |
| 15  | ACTAGTACGCTCCCG | 115 | CGTCGGACCGCTAGT | 215 | TACGACTAGCCCGGT |
| 16  | ACTAGTCGCGGCTAC | 116 | CGTCGTACTAGGGTC | 216 | TACGCCCGTAGCTTA |
| 17  | ACTAGTCGGTACCCG | 117 | CGTCTAACTAACCGC | 217 | TACGCCGGTTAGACT |
| 18  | ACTTACGCCCTATCG | 118 | CGTCTACTAGTCGGA | 218 | TACGCCTAGGGGCGA |
| 19  | ACTTACGCGGTCCTA | 119 | CGTTACTACGTAGCG | 219 | TACGCGCCGTCTAAC |
| 20  | ACTTAGCGGTCGCGT | 120 | CGTTAGTACGCGGTC | 220 | TACGCGCCTTAGGGT |
| 21  | AGCGCGCTAGTCCGT | 121 | CGTTTAGCGGTCTAC | 221 | TACGCGGAACCTAGG |
| 22  | AGCTAGGCGCGTTAC | 122 | CTAACTAAGTTCGCG | 222 | TACGCGTACTAGCCC |
| 23  | AGGCGCGAACTAGTA | 123 | CTACGCGTAGGTTGG | 223 | TACGCTAAGTCGGGC |
| 24  | AGTCTAACCGGCGTA | 124 | CTACGGCGTATAGGG | 224 | TACGCTAGCCCGTGG |
| 25  | AGTTAGGCCCGACGC | 125 | CTACGGGCGTAGTA  | 225 | TACGCTAGGTCGGAT |
| 26  | ATACTAGACCGCTCG | 126 | CTACGGGTAGACCGA | 226 | TACGCTAGTTCCGGG |
| 27  | ATACTAGCGTCGGAC | 127 | CTAGACGCCCGTATA | 227 | TACGGGCCTAACCGT |
| 28  | ATAGCCGCGGTCCTA | 128 | CTAGATCGTACCCCG | 228 | TACGGGCGTCTAGTA |
| 29  | ATAGCGCGTTAGGAC | 129 | CTAGCCCGATACGCG | 229 | TACGGGGCGTCCCTA |
| 30  | ATCCGACCTAGCGTA | 130 | CTAGCGCGATACGGG | 230 | TACGGGTCGCTAGGG |
| 31  | ATTAGGCCCGCGATC | 131 | CTAGCGGGGACTACG | 231 | TACGTACAACGCGGG |
| 32  | CATCGGACTAGTACC | 132 | CTAGCGTACGCTACG | 232 | TACTACGCCCCGTAG |
| 33  | CCAACCTACGCGTAG | 133 | CTAGGCGCGATATCC | 233 | TACTAGACGCCCGTA |
| 34  | CCACGGGCTAGCGTA | 134 | CTAGGTTACCGATCG | 234 | TACTAGACTTCCGCG |
| 35  | CCATACGCCTAGTCG | 135 | CTAGTAACTCGCGGC | 235 | TACTAGGCGACTCGA |
| 36  | CCCCGTACTAGCGGA | 136 | CTAGTACGGACCGCG | 236 | TACTAGTTCGCGCCT |
| 37  | CCCCGTAGCGAACTC | 137 | CTAGTCCCTACGCGG | 237 | TACTTAGGTCCGCGA |

TABLE 2-continued 15 base primes as of 2007
(note: the nucleotide compliments of these sequences are also primes). Shading indicates sequences used in the example 2 below.

| # | Sequence | # | Sequence | # | Sequence |
|---|---|---|---|---|---|
| 38 | CCCGACTTAAGAGCG | 138 | CTAGTCGGACCGTAC | 238 | TAGACCTAGCGCGGA |
| 39 | CCCGCATACGACTAG | 139 | CTAGTCGGTACGGGC | 239 | TAGCGCGAACTAGGT |
| 40 | CCCGCGTTGTACGTA | 140 | CTAGTCGTATGCGGG | 240 | TAGCGGACGGTCCTA |
| 41 | CCCGCTAGCGAAGTT | 141 | CTAGTCGTCCGGGTA | 241 | TAGGACCGCGGCTAT |
| 42 | CCCGGAACTAGCGTA | 142 | CTCTATAGTCGGACG | 242 | TAGGACCGCGTAAGT |
| 43 | CCCGTATCGCGCTAG | 143 | CTTAACGGTCCTACG | 243 | TAGGACCGTCCGCTA |
| 44 | CCCGTTACGCGACTA | 144 | CTTAGATTAGCGACG | 244 | TAGGACGCGACTAAG |
| 45 | CCCTAACGCGTACTA | 145 | CTTAGGGCGTTACGC | 245 | TAGGGACGCCCCGTA |
| 46 | CCCTACGTCGTAGCG | 146 | CTTAGTCGCGTCCTA | 246 | TAGGGACGTTCCGCG |
| 47 | CCCTAGCGACCCGTA | 147 | GAACTAGCCTACGCG | 247 | TAGGGCGTCCTACCG |
| 48 | CCCTATACGCCGTAG | 148 | GACCCTACGCGTAGT | 248 | TAGGGCTACGCACCG |
| 49 | CCGCGTAGGGACTAG | 149 | GACCCTAGTACGACG | 249 | TAGGTCCGCGTAACC |
| 50 | CCGGGCGTAGCTAAC | 150 | GACCGCGTACTAACG | 250 | TAGGTCTATGCGCGA |
| 51 | CCGGTGTACTAACGC | 151 | GAGTTCGCTACGGGG | 251 | TAGGTTAGCCGTACG |
| 52 | CCGTACTAAGGGCGC | 152 | GATCGCGGGCCTAAT | 252 | TAGTACGATCCCCCG |
| 53 | CCGTACTACGGCTTA | 153 | GCCCGACTTAGCGTA | 253 | TAGTACGCCTCCCGA |
| 54 | CCTAGGTTCCGCGTA | 154 | GCCCGTACCGACTAG | 254 | TAGTACGCGTTAGGG |
| 55 | CCTAGTACGACCCGC | 155 | GCCGCGAGTTACTAG | 255 | TAGTCCGCCCTACGA |
| 56 | CCTAGTACGTTACGA | 156 | GCGCCCTTAGTACGG | 256 | TAGTCGCGTAACGGG |
| 57 | CCTAGTATACGCCCG | 157 | GCGCGAGACGTTAGT | 257 | TATACGGGCGTCTAG |
| 58 | CCTAGTCGCGTAGAC | 158 | GCGCGATAGGTCTAA | 258 | TATCTATACGCGGCC |
| 59 | CCTTAGACGCGGTCG | 159 | GCGCGTCCTATCAAC | 259 | TATTAGCGGGACCCG |
| 60 | CCTTAGTGCGACCCG | 160 | GCGCTTAGACGGGTA | 260 | TCCGACTAGTAGACG |
| 61 | CGAATCTAGGCGGAC | 161 | GCGGGTCGTACTAGG | 261 | TCCGCGCTAGGTCTA |
| 62 | CGACCGCGTCTAAGG | 162 | GCGGTTAGTTAGACG | 262 | TCCGCGGTTAGTTAC |
| 63 | CGACTAAGCATACCG | 163 | GCGTAACGCCCTAAG | 263 | TCCGCTAGTACGGGG |
| 64 | CGACTAGGCGTATGG | 164 | GCGTCCGTAGTCTAC | 264 | TCGAGTCGCCTAGTA |
| 65 | CGAGCGGTCTAGTAT | 165 | GCGTCGGGCCTAACT | 265 | TCGCCCCTAGGCGTA |
| 66 | CGATAGGGCGTAAGT | 166 | GCGTTAGACTATCGT | 266 | TCGCGACTTAGGCCC |
| 67 | CGATAGTCTAACGCG | 167 | GCGTTAGTACACCGG | 267 | TCGCGCATAGACCTA |
| 68 | CGATCGGTAACCTAG | 168 | GCTAGTCCGCGTACG | 268 | TCGCGGACCTAAGTA |
| 69 | CGCCTAGTTCCGTAC | 169 | GGACTAATCTACGCG | 269 | TCGCGTTAGGTACCC |
| 70 | CGCGAACTTAGTTAG | 170 | GGACTATCGTACGCG | 270 | TCGGCGTACTAACGT |
| 71 | CGCGCGTATTAGACC | 171 | GGATATCGCGCCTAG | 271 | TCGGGAGGCGTACTA |
| 72 | CGCGGAACGTCCCTA | 172 | GGCCGCGTATAGATA | 272 | TCGGTCTACCCGTAG |
| 73 | CGCGGAAGTCTAGTA | 173 | GGGCCTAAGTCGCGA | 273 | TCGTAACGTACTAGG |
| 74 | CGCGGACGCTAGTTA | 174 | GGGCTAGTACGCGTA | 274 | TCGTAGGGCGGACTA |
| 75 | CGCGGTCCGTACTAG | 175 | GGGTACCTAACGCGA | 275 | TCTAACGCGACGTTA |

TABLE 2-continued 15 base primes as of 2007
(note: the nucleotide compliments of these sequences are also primes). Shading indicates sequences used in the example 2 below.

| # | Sequence | # | Sequence | # | Sequence |
|---|---|---|---|---|---|
| 76 | CGCGTAACCCTACGT | 176 | GGGTCCGGTCTTACG | 276 | TCTAGGCGTACCGAC |
| 77 | CGCGTACGATAGTCC | 177 | GGTACTAGTCCGATG | 277 | TCTAGTAGCGCGACC |
| 78 | CGCGTAGATTAGTCC | 178 | GGTCGCGCTACTAGA | 278 | TGCGACCCGTCTTAC |
| 79 | CGCGTAGCGGACTTA | 179 | GGTCTAATACGCGCG | 279 | TTACGCGTAGGTCCG |
| 80 | CGCGTAGGCTAGTTC | 180 | GGTTACGCGGACCTA | 280 | TTACTAGTCGCGCGT |
| 81 | CGCGTATCGGGCTAG | 181 | GTAACGCGCCTAGCT | 281 | TTAGACCTATCGCGC |
| 82 | CGCGTTAGACTATCG | 182 | GTAACTAACCGCGGA | 282 | TTAGGCCGTCCTACG |
| 83 | CGCTACGACGTAGGG | 183 | GTAAGACGGGTCGCA | | |
| 84 | CGCTACGTAGTAACG | 184 | GTACGGAACTAGGCG | | |
| 85 | CGCTAGTACGCGAAC | 185 | GTACGGGCGCTAGAC | | |
| 86 | CGCTCTTAAGTCGGG | 186 | GTACGGTCCGACTAG | | |
| 87 | CGGACCTACGCGTAA | 187 | GTAGACCGCTAAACG | | |
| 88 | CGGGACTATCCTACG | 188 | GTAGACTACGGACGC | | |
| 89 | CGGGAGCGTACTAGT | 189 | GTAGCCGCGACTAGT | | |
| 90 | CGGGCGTATACTAGG | 190 | GTCCGACGCTAGTAT | | |
| 91 | CGGGGGATCGTACTA | 191 | GTCCGCCTAGATTCG | | |
| 92 | CGGGGTACGATCTAG | 192 | GTCCGCGCTACGTTA | | |
| 93 | CGGGTACCGACTAGT | 193 | GTCCTAACGCGCTAT | | |
| 94 | CGGGTCCCGCTAATA | 194 | GTCGGTACGCCTAGA | | |
| 95 | CGGGTCGCACTAAGG | 195 | GTCTACGCGACTAGG | | |
| 96 | CGGTACGTACTAGAC | 196 | GTCTAGACCGCGTTA | | |
| 97 | CGGTAGGACGCCCTA | 197 | GTCTAGCGCCCGTAC | | |
| 98 | CGGTATGCTTAGTCG | 198 | GTCTAGTACGTACCG | | |
| 99 | CGGTCGTACTAACCG | 199 | GTTACGCGTAGACCG | | |
| 100 | CGGTCTACGCGTAAC | 200 | GTTAGACGGCGCGTA | | |

*the number preceding each sequence is the SEQ ID NO: for that sequence.

In another embodiment, the invention encompasses synthetic oligonucleotide primers and probes that hybridize to the oligonucleotides described herein, such as those presented in Tables 1 or 2, or RMs which comprise the oligomers listed in Tables 1 and 2. Those of skill in the art are familiar with techniques for designing primers and probes with properties suitable for use in DNA sequencing or other nucleic acid analysis techniques, including considerations of annealing properties, Tm values, etc. In a preferred embodiment, the primers hybridize under stringent conditions to these oligonucleotides. Another embodiment provides oligonucleotide probes capable of hybridizing to the oligonucleotides described herein, for example, oligonucleotide RMs comprising one or more copies of one or more of the sequences as listed in Tables 1 and/or 2. The polynucleotide primers or probes include at least about 10-50 bases, e.g. at least about 10, 15, 20, 25, 30, 35, 40, 45 or 50 or more bases. In some embodiments, the primers have about 14 bases, or 20 bases, preferably 30 bases or 50 bases which hybridize to a polynucleotide RM of the present invention. The probe or primer can be at least 14 nucleotides in length, and in a preferred embodiment, are at least 15, 16, 17, 18, 19, 20, 21, 22, 23, 24, 25, 26, 27, 28, 29, or 30 nucleotides in length.

The oligonucleotide RMs and the primers and probes of the present invention can be synthesized by any technique known to one skilled in the art. For example, the phosphoramidite method can be used.

III. Construction of RMs

The reference markers of the present invention can be synthesized by any technique known to one skilled in the art. In one embodiment, the primes can be used as a starting material to synthesize a longer reference marker. For example, combinations of various nullomer and/or prime sequences can be generated that can be amplified without interfering with primers used in human identification, and without the risk of amplifying sequences commonly found in evidentiary samples, such as DNA from domestic plants and animals. The RMs for human identification are generally of a length in the range of from about 30 to about 600 nucleotides in length, or from about 70 to about 150 in length, and are preferably of a length of from about 80 to about 120 nucleotides in length. Generally, an RM will comprise from at least about 2 to about 4 prime or nullomer sequences, or from at least about 5 to about 10 prime or nullomer sequences, or from at least about 11 to about 50 or more prime or nullomer sequences. Within an RM, the nullomer and/or prime sequences may be arranged in tandem immediately adjacent to and abutting each other, or the sequences may be separated by linker or spacer sequences. Further, an RM may contain a single (i.e. one) type of nullomer and/or prime sequence (e.g. one sequence from Table 1 or 2, or one sequence repeated several times) or may contain a mix or combination of many different prime and/or nullomer sequences, each of which may be used once or multiple times. In addition, sequences such as restriction enzyme cleavage sties, methylation sites, protein binding sites, transcription promoter sequences, siRNA coding sequences, customized coding information (for date, location, sample type etc), individualized nucleotide tagging sequences, etc., may also be included. Based on the sequences of nullomers and/or primes, RMs can be synthesized for use in conjunction with kits employed in forensic, paternity, human, biotechnology, animal, plant, bacterial, viral and other identification applications. Such kits are well known in the art, and are commercially available from sources such as Applied Biosystems of Foster City, Calif. and Promega of Madison, Wis.

IV. Detection of the RMs

For authenticating or tagging a sample of interest, RMs are added to the sample (or to a container that contains or will contain the sample). In one embodiment 10 to 100 copies of the marker are added to a sample. In another embodiment 100 to 1000 copies of the marker are added to a sample. In another embodiment 1,000 to 10,000 copies of the marker are added to a sample. In another embodiment 10,000 to 100,000 copies of the marker are added to a sample. The RM that is added may be of a single type (i.e. all RMs that are added have the same sequence) or, alternatively, multiple types of RMs with differing sequences may be added to the sample, providing an even higher level of specificity and/or security. Those of skill in the art will recognize that, if multiple types of RMs are used in the practice of the invention, and if PCR amplification is used for detection of the RMs, then multiple primer sets will likely be used for detection, although this need not always be the case, depending on the precise sequence of the RM.

In one embodiment, the RMs will yield amplicons of at least about 10, 20, 30, 40, 50, 60, 70, 80, 90, 100 base pairs. In one embodiment the amplicon can be below the size of any common human allele used in STR profiling, for example less than about 90, 80, 70, 60, 50, 40 base pairs. In another embodiment the amplicon can be above the size of any common human allele used in STR profiling, for example more than about 450, 480, 500, 550, 600, 650 base pairs. In a further embodiment, the RM can be detected by DNA sequencing. In another embodiment, the RM can be detected by SNP analysis. In further embodiments, the RM can be identified using PCR, isothermal nucleic acid amplification (such as that used by biohelix, Beverly, Mass.), pyrosequencing, GC/MS, or other methodology.

PCR is based on the use of two specific synthetic oligonucleotides which are used as primers in the PCR reaction to obtain one or more DNA fragments of specific lengths. The test can detect the presence of as little as one DNA molecule per sample, giving the characteristic DNA fragment. Polymerase chain reaction (PCR): a technique in which cycles of denaturation, annealing with primer, and extension with DNA polymerase are used to amplify the number of copies of a target DNA sequence by $>10^6$ times.

In general, PCR can be performed according to the following protocol (adapted from U.S. Pat. No. 4,683,195). The specific nucleic acid sequence is produced by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical or enzymatic means. One physical method of separating the strands of the nucleic acid involves heating the nucleic acid until it is completely (>99%) denatured. Typical heat denaturation can involve temperature ranging from about 80 degrees to 105° C. for times ranging from about 1 to 10 minutes. Strand separation can also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63-67, and techniques for using RecA are reviewed in C. Radding, Ann. Rev. Genetics, 16:405-37 (1982). If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis can be performed using any suitable method. Generally it occurs in a buffered aqueous solution, preferably at a pH of 7-9, most preferably about 8. Preferably, a molar excess (for cloned nucleic acid, usually about 1000:1 primer: template, and for genomic nucleic acid, usually about $10^6$:1 primer:template) of the two oligonucleotide primers is added to the buffer containing the separated template strands. It is understood, however, that the amount of complementary strand can not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP and TTP are also added to the synthesis mixture in adequate amounts and the resulting solution is heated to about 90 degrees-100 degrees Celsius for from about 1 to 10 minutes, preferably from 1 to 4 minutes. After this heating period the solution is allowed to cool to from 20 degrees-40 degrees Celsius, which is preferable for the primer hybridization. To the cooled mixture is added an agent for polymerization, and the reaction is allowed to occur under conditions known in the art. This synthesis reaction can occur at from room temperature up to a temperature above which the agent for polymerization no longer functions efficiently. Thus, for example, if DNA polymerase is used as the agent for polymerization, the temperature is generally no greater than about 45° C. An amount of dimethylsulfoxide (DMSO) can be present which is effective in detection of the signal or the temperature is 35 degrees-40 degrees Celsius. In one aspect of the invention, 5-10% by volume DMSO is present and the temperature is 35 degrees-40 degrees Celsius. For certain applications, where the sequences to be amplified are over 110 base pair fragments, an effective amount (e.g., 10% by volume) of DMSO is added to the amplification mixture, and the reaction is carried out at 35 degrees-40 degrees Celsius, to obtain detectable results or to enable cloning.

The agent for polymerization can be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heat stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There can be agents, however, which initiate synthesis at the 5' end and proceed in the other direction, using the same process as described above.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional inducing agent, nucleotides and primers can be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers.

The steps of strand separation and extension product synthesis can be repeated as often as needed to produce the desired quantity of the specific nucleic acid sequence. As will be described in further detail below, the amount of the specific nucleic acid sequence produced will accumulate in an exponential fashion.

When it is desired to produce more than one specific nucleic acid sequence from the first nucleic acid or mixture of nucleic acids, the appropriate number of different oligonucleotide primers is utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process. The polymerase chain reaction process for amplifying nucleic acid is described in, for example, U.S. Pat. Nos. 4,683,195, 4,965,188 and 4,683,202, the complete contents of each of which are hereby incorporated by reference, and European patent Nos. EP 201184 EP 200362.

DNA samples are subjected to PCR amplification using primers and thermocycling conditions specific for each locus that contains a sequence of interest, e.g. an RM as described herein. In one example, the primers are selected from the group of sequences shown in Tables 1 and 3. The specific amplification procedures and primer sequences relating to each locus and allelic ladder, as well as a description of locus-specific primers are described in U.S. Pat. Nos. 6,156,512 and 5,192,659, the complete contents of each of which are hereby incorporated by reference.

V. Application of RMs to Substrates and Containers

In one embodiment, the RMs can be added to a solid substrate or container, for example, the collection substrates of kits used for sample collection, such as in forensic or medical applications. Such kits are available in a number of forms and include various substrates for samples. The RM molecules can be added directly to a component of the kit which is suitable for receiving a nucleic acid sequence. This component is generally the same as or similar to a component that will also receive the unknown DNA sample that is being authenticated. One exemplary kit is the FTA® classic card, manufactured by Whatman, plc, Brentford, Middlesex, UK. Kits of this type include FTA® paper to which the RMS may be added, either during manufacture or subsequently. The RMs can be applied as an aqueous solution, powder, gel, laminate, spray, resin, etc. or in a form such as a capsule, or in any other suitable form. RMs may also be coated or spotted onto the walls of a collection container, or impregnated into a swab or other component of a kit.

In another embodiment, the RMs can be added e.g. to a liquid in the collection vessel such as the Vacutainer System of Becton, Diskinson and Company, Franklin Lakes, N.J.

In another embodiment, the RMs can be combined with agents or processes used in sample preparation, storage or processing, e.g. agents that are used to protect DNA samples at room temperature.

VI. Kits

In other embodiments of the present inventions, kits are provided that include the oligomers and/or reference markers of the present invention. In addition, the kits can include applicator sticks, swabs, tubes, membranes, cotton, nylon, FTA® paper, locking mechanisms, vessels, chambers, buffers, fixatives, drying agents, labels, bar codes, needles, microneedles, pins, lances, anticoagulants, EDTA, heparin, preservatives, primers, magnesium, DTT, dyes, antibodies, alcohol, extraction buffer, phenol, chloroform, proteinase K, SDS, etc. or any other suitable components.

The invention thus also provides kits containing a reference oligonucleotide marker, wherein the oligonucleotide sequence of the RM does not overlap with a nucleotide sequences reported in the human genome (or other genome(s) in publically available databases of natural species), which is deposited in or on a container. In one embodiment the kit also contains a self-locking system, wherein the swab used for buccal scraping is broken off from the applicator stick and deposited in a self sealing tube which contains the reference marker.

The RMs described herein may be used for any of a number of applications in which nucleic acid analysis is involved. The nucleic acid analysis is frequently DNA sequencing. The applications include but are not limited to, for example: forensic/crime investigations; paternity investigations; medical applications; archeological investigations; verifications of the identity of living or deceased subjects or of remains of subjects; investigations of genealogical bloodlines (e.g. of "prize" animals, or of the ancestry of a human or humans, either recent genealogies or so-called "deep" ancestry extending into prehistoric times; testing of food or other items for contamination (e.g. for a source of food poisoning, for chemical contaminants, etc.) or for any investigation which involves the collection of nucleic acid samples or samples and their subsequent analysis, especially in cases where it is important to verify or authenticate or track the origin of a sample, e.g. to establish that the sequence of a sample is accurately attributed to or associated with the actual source of the sample. Generally, samples that are analyzed using the methods described herein are known to contain or suspected of containing genomic DNA from an organism or individual of interest, although this may not always be the case. Other applications for this technology also exist, including but not limited to: the use of the oligomers to authenticate samples intended for analysis with respect to contamination, e.g. by microbes, such as water, food samples, etc.; the use of the oligomers to authenticate samples of substances which are intended for analysis with respect to chemical contamination; the use of the oligomers to label and trace or track manufactured goods (e.g. synthetic oligonucleotides, synthetic genes, synthetic genomes or portions thereof, vectors, etc.); samples of naturally occurring or genetically engineered organisms (bacteria, algae, fungi, cultured cells, etc.); or articles or items that have nothing to do with nucleic acids per se (e.g. food items, various liquids, textiles, household goods, etc.), providing the manufacturing and storage or use of the product does not destroy the integrity of the RMs, and so long as the RMs remain detectable in a reliable manner within or associated with the product.

EXAMPLES

Example 1

Identification of 11 and 12 Base Nullomers

The human genome has been searched using an iterative algorithm which looks for the smallest sequences not found in the selected genome. Our results are presented in Table 1 for the two publicly available human genome sequences. The oligomer sequences not found in the selected genome are called nullomers. The complete set of 11 and 12 base nullomers for the human genome have been determined using this method. These sequences can be used to construct artificial genomes, or genetic elements such as tags, novel protein epitopes, and novel RNA sequences and structures, not found in the human genome. The human nullomers were then used for BLAST searches with the goal of identifying: those sequences which were not represented in any living organism, those that were rare (represented less than 5 times in all the publicly available sequences), those not found in mammals, those not found in eukaryotes, those not found in viruses, those not found in plants, those not found in bacteria; and those not found in combinations of these organism groups. These sequences can be used to construct artificial genomes, or genetic elements such as tags, novel protein epitopes, and novel RNA sequences and structures, not found in the known sequences of the biosphere.

In one embodiment, the reference markers (RMs) will yield amplicons of about 60 base pairs, below the size of any common human allele found in STR profiling. One example of an amplicon generated by amplification of an RM-based nullomer tag is cgacgtatcgg accgttcgtcg ccgatacgtcg cgacgaacggt tacgctcggac gtccgagcgta cgctcgacgta (SEQ ID NO: 369).

Example 2

Unintended transfer of biological samples is an issue of great concern to all laboratories conducting sensitive analysis. This is particularly true for crime laboratories, where victims and suspects are asked to supply reference samples of their DNA for comparison to evidence profiles. Contamination, or unintended transfer, can happen at any time in forensic DNA analysis, from before sample collection until entry into the database. Instances of unintended transfer, and mislabeling by personnel collecting and processing samples, are well documented. This problem is likely to become more pronounced as forensic DNA techniques become ever more sensitive. Laboratories which use enhanced techniques for low template DNA analysis have detected contamination in reagents, plastic ware and laboratory samples at levels that are below detection with less sensitive methods. Likewise, secondary and tertiary transfer of DNA that was previously below detection limits is now more readily seen with techniques that can produce profiles from just a few cells. Finally, because laboratory protocols amplify molecular targets millions of times over, extreme caution must be taken to isolate amplified DNA from all areas where evidence processing occurs. Even a million-fold dilution of amplified DNA contains enough template in a fraction of a microliter to cause contamination.

In order to safeguard against the accidental or malicious transfer of DNA samples collected from members of the public, we have developed a universal tag that can be modified to code a variety of information, such as laboratory location, testing purpose, or date. These tags are based on the smallest sequences absent from all publicly available DNA databases (nullomers). The nullomer approach has generated interest in algorithms for counting and tracking biological sequences, and several researchers have recently proposed efficient methods for determining the set of shortest absent sequences, and the set of minimal absent sequences. The algorithm used to identity the nullomers and primes described herein is able to process the entire set of biological sequence data found on NCBI's web site in less than 8 hours, calculating the frequencies of all sequences up to length 17 (longer lengths can be calculated as well). At length 17 there are (as of January 2011) approximately 700 million (695,038,288) absent sequences.

This Example describes the first practical application of nullomer sequences. The results show that nullomer sequences can be used as molecular barcodes, successfully integrated into the multiplex PCR reactions of commercially available forensic profiling kits, and used along with PCR for sequencing.

Methods

Nullomer Barcode Identification

Candidate nullomer sequences for barcodes were identified by examining all of the DNA sequence data available from the National Center for Biotechnology Information (NCBI) website using a robust software algorithm we developed for this purpose (Hampikian, G. & Andersen, T. Absent sequences: nullomers and primes. Pac Symp Biocomput, 355-366 (2007); the complete contents of which are hereby incorporated by reference). The algorithm, which is capable of processing the entire data set in about 8 hours, counts the number of possible sequences up to a maximum specified length, and outputs the sequences that have a zero count. Currently, there are approximately 700 million DNA 17-mers that have a zero count, i.e. are not found in any of the DNA data available from NCBI (and 2,358,580 absent 16-mers as well as 34 absent 15-mers), which makes it possible to construct an enormous number of unique DNA based tags using relatively short sequences.

Nullomer Barcode Construction

To construct the barcodes for our experiments, eight 15-mer nullomer sequences were arranged in tandem. Sequences were chosen to minimize the formation of secondary structure, by running sequences in the OligoAnalyzer tool on the Integrated DNA Technologies (IDT) website located at www.idtdna.com. Terminal sequences (primer binding regions) were chosen so that the annealing temperature would match as closely as possible the 59° C. annealing temperature of the ABI kit protocols (58° C. for Powerplex-Y kit). The 120 bp construct was synthesized by IDT (Coralville, Iowa, USA) as two complimentary single stranded molecules. This complimentary pair was annealed to make it double stranded, using a thermal gradient from 95° C. to 75° C. After annealing the nullomer strands, ExoSAP™ enzyme treatment was used to cleave all the remaining single stranded molecules. Primers were designed to yield amplicon sizes of 88, 90, and 114 bp. Several barcode concentrations were tested with different STR kits; results are presented using 1,900 copies per PCR reaction, which gave barcode peaks at intensities comparable to the human STR alleles.

Real-Time PCR Quantification

For DNA quantification a DNA dilution series was made, according to the manufacturer's protocol, with the male genomic DNA standard supplied with the Duo kit. The nullomer barcode (without barcode primers) was added to each of the qPCR reactions. PCR was performed on an Eppendorf Mastercycler realplex instrument and data analyzed with Realplex software and GraphPad Prism 5 software.

STR and Y-STR Amplification

The compatibility of nullomer barcodes was tested with STR kits from ABI (Identifiler™, Yfiler™, Profiler Plus™) and Promega (Yplex™). The Profiler Plus™kit amplifies 10 loci, and the Identifiler amplifies 16 loci (including amelogenin). The Yfiler™ kit amplifies 17 Y-STR loci, and Yplex™ amplifies 11 Y-STR loci. For STR reactions, ABI and Promega's standard protocols were strictly followed, e.g. thermal cycling, reaction buffer, and primer mix concentrations. Approximately 1,900 nullomer barcode amplicons were added to each 1 ng human DNA samples extracted from buccal swabs. Barcode primers were at 2.5 µM final concentration per PCR reaction. The amplicons were analyzed in an ABI 3130 genetic analyzer, with Pop-4™ polymer, using Gene Mapper ID-X software.

Human Mitochondrial DNA Sequencing

Three different concentrations of nullomer barcode molecules were added to sequencing reactions: 962, 1900, and 3800 copies. Amplicons were visualized on a 3% agarose gel to verify both bands present (HV1 and HV2), along with the nullomer barcode bands. For sequencing reactions, nullomer barcodes were added to the reactions but not the barcode primers. Pop-4™ polymer and Big Dye 3.1® terminator chemistry were used for sequencing. PCR products were purified by ExoSap (USB) kit and also with the Bigdye® XTerminator™ kit (ABI) before sequencing. 3-10 ng DNA were used for each cycle sequencing reaction. Both the HV1 and HV2 control regions were analyzed to verify that the nullomer barcode did not interfere with mitochondrial sequencing reactions.

DNA Extraction from Swab and FTA Paper

Approximately $1.5 \times 10^8$ copies of the barcodes were dissolved in 100 µl of double distilled water applied to 572.6 mm$^2$ FTA paper (Fitzco Inc, Minnesota, USA), and allowed to dry overnight. Then cells from a male and female donor's buccal swabs were applied to the FTA paper by gently rubbing each swab against the card. Five punches (2 mm diameter) were taken from each FTA card. Assuming an even distribution of nullomer barcode solution, we estimate that each punch had approximately $1.5 \times 10^7$ copies of the nullomer barcode. DNA extraction was performed using Qiagen's DNA Mini kit (according to manufacturer's protocol). The amount of total extracted DNA was quantified on a Nanodrop ND-1000. Quantification was visually checked by agarose gel electrophoresis with Lonza's quant ladder, and visualized with a Gel Doc XR imager (BIO-RAD) using Quantity One 4.6.5 software (BIO-RAD). One nanogram of extracted DNA was used to generate a profile using the Identifiler kit supplemented with forward and reverse barcode primers.

Mock "unintended transfer" of amplified DNA to a knife in the laboratory DNA was extracted from a buccal swab (Whatman sterile OmniSwab), transferred to FTA paper containing the nullomer barcode (as above) and amplified with ABI's Identifiler kit. All reactions were processed according to manufacturer's instructions with the addition of the nullomer primers to the PCR reaction. After STR amplification, 1-10 µl of post amplified DNA was applied to several knives to see the abundance and stability of nullomer barcodes. Post PCR reactions were also diluted 100,000, and 1,000,000 times before applying to the knife and swabbing. Each knife was swabbed with a sterile omniswab, and DNA was extracted with Qiagen's DNA mini kit using a 15 minute, 56° C. incubation in the extraction buffer. The extracted DNA was amplified with the Identifiler™ kit.

Sequences for Nullomer RMs (barcodes) and primers used in this study were as follows:

```
Nullomer Barcode
                                                      (SEQ ID NO: 370)
5'-TAC TAG GCG ACT CGA CGG TCT TAC GCG TTA CGT CCG ACT ATA GAG

CTT AGA TTA GCG ACG TTA GAC CTA TCG CGC CTT AGA TTA GCG ACG

CTA GCG TAC GCT ACG GTC CTA ACG CGC TAT-3';

Primer_114F
                                                      (SEQ ID NO: 371)
5'-TAG GCG ACT CGA CGG TCT TAC GCG TTA CGT;

Primer_114R
                                                      (SEQ ID NO: 372)
5'-GCG CGT TAG GAC CGT AGC GTA CGC TAG CGT;

Primer_88F
                                                      (SEQ ID NO: 373)
5'-TAC TAG GCG ACT CGA CGG TC;
```

-continued

```
Primer_88R
                                                         (SEQ ID NO: 374)
5'-TCG CTA ATC TAA GGC GCG ATA GGT C;

Primer_90F
                                                         (SEQ ID NO: 375)
5'-TAC TAG GCG ACT CGA CGG TC;

Primer_90R
                                                         (SEQ ID NO: 376)
5'-CGT CGC TAA TCT AAG GCG CGA;

Prime 108 R (108 bp product when paired with Primer_F_114)
                                                         (SEQ ID NO: 377)
5'-TAG GAC CGT AGC GTA CGC TAG CGT CGC TAA.
```

Results

Adding the nullomer tag to a human buccal swab did not affect the quantification of extracted DNA (FIG. 1A). The kit used in our experiment (Quantifiler® Duo) is commonly employed by forensic laboratories to determine the DNA concentration for both the total human and male fraction (Y-chromosome) of a sample. The data presented here shows that the nullomer tag does not negatively impact either quantification. We designed the barcode DNA amplicons to be a size outside the range of human alleles, so that there is no confusion between the barcode and known STR allele peaks. When amplified with the STR alleles of the forensic kits we tested, a 90 base pair nullomer barcode appears in the electropherogram as an additional peak outside the first bin set. Human DNA and barcode DNA was amplified according to manufacturer protocols (except for the addition of the nullomer barcode and barcode primers) with several standard techniques. Exemplary results obtained with Identifiler™ are presented in FIG. 2. Similar successful results were obtained using Profiler Plus™, Yfiler™, and YPlex™ kits. A number of different nullomer-based primer sets have been created for applications that may benefit from larger or smaller tags. The results for an 88 base pair and a 114 base pair amplicon using the Identifiler™ kit showed that amplification was successful and the barcod RMs were readily distinguishable (not shown) We also demonstrated that the addition of a nullomer-specific primer set is required, and that the nullomer barcode cannot be amplified with STR primers alone (FIG. 3). Therefore, the addition of these barcodes does not affect the typical analysis of forensic DNA.

A common technique for the storage and processing of reference samples is to transfer a buccal swab sample to FTA paper and allow it to dry. DNA samples fixed onto FTA paper can be stored at room temperature, and then be extracted from FTA paper punches when needed. When we extracted and amplified DNA from nullomer-treated FTA paper, we obtained a profile which includes the barcode tag, identifying the DNA as coming from a reference source (FIG. 4), and not from evidence.

Figure 1B:
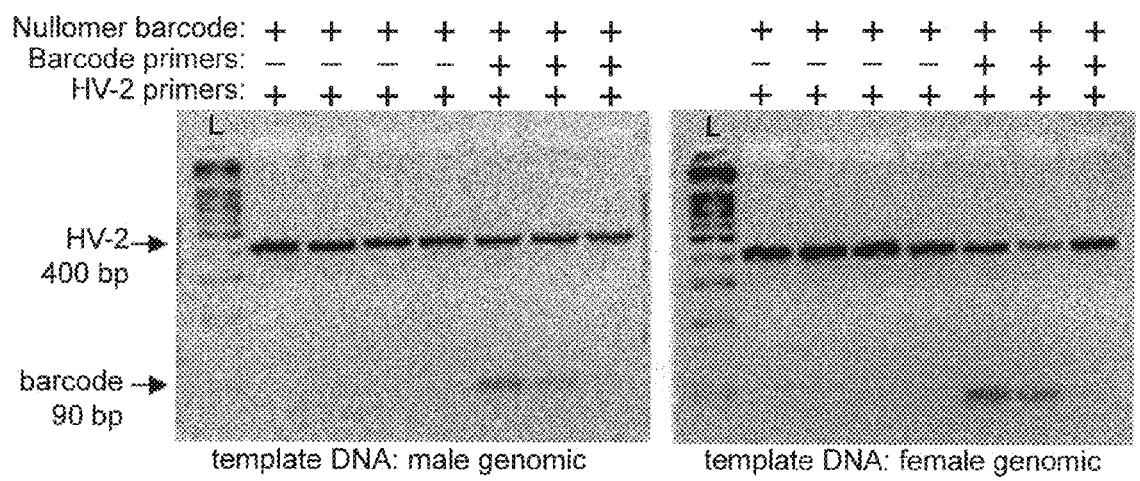

In order to test whether our nullomer tag is compatible with mitochondrial DNA (mtDNA) sequencing, we amplified the HV-1 and HV-2 regions of human mtDNA in the presence of nullomers, with and without tag primers. The barcode PCR products were detected as distinct bands in a 3% agarose gel (FIG. 1B and FIG. 5). Mitochondrial DNA sequencing was not adversely affected by the presence of the nullomer barcode, whether the barcode was added during initial PCR using HV1 and HV2 primer sets, or during sequencing reactions using HV1 or HV2 amplicons as templates (FIG. 6).

We setup a mock unintended transfer of Identifiler amplified DNA (with barcode) to an evidentiary weapon (knife). A 105-fold dilution of the PCR product showed clear amplification of nullomer barcode DNA along with a partial profile of the transferred human amplicons (FIG. 7A). After a 106-fold dilution, the nullomer barcode could be detected; even though the human profile was lost (FIG. 7B).

We have shown that an artificial DNA barcode can be used in conjunction with forensic genetic analysis kits, without affecting DNA quantification, STR amplification, profile determination, or mitochondrial sequence, using standard protocols. DNA profiles were obtained by amplification of 0.5-1.0 nanograms of genomic DNA in the presence of 500-8000 copies of nullomer barcodes. The nullomer barcodes can used to pre-treat FTA paper, and we envision nullomer-tagged FTA kits, which would mark samples without affecting forensic DNA profiling.

Extrinsic DNA can enter the laboratory through contaminated reagents, disposables, centrifuges and water baths. Reagent controls and routine monitoring can detect many of these examples, however, contamination of evidence with DNA from reference samples taken from suspects, or the switching of reference samples, is more difficult to detect, and may in fact implicate an innocent person in a crime. The nullomer tags described in this paper were developed to assure the public that their reference samples can be marked so as to prevent false incrimination. Further development of the tag technology can be used to code individual samples to further safeguard the public. The initial tags described here can be added to collection kits so that reference samples are safeguarded from the point of collection, through handling by the collector, laboratory processing and storage, amplification, and even post amplification. Physical and chemical modifications of the tags could be used to stabilize them further; though we demonstrate here that even unmodified synthetic DNA is sufficient. While the barcode is not designed to detect environmental contamination, it will detect contamination or mislabeling involving reference and evidence samples processed in the same lab. The barcodes have been stored at 4° C. for one year in TE buffer without affecting amplification and detection, and used FTA paper with dried barcodes has been used for six months without any noticeable effect on amplification.

Synthetic DNA barcoding has been used to make positive amplification controls for applications in a wide variety of fields, such as clinical microbiological testing and food pathogen testing, and has been discussed for a broad variety of tagging and tracing protocols; but unlike nullomer tagging these methods do not build their artificial sequences from combinations of the smallest sequences absent from public databases. While these sequences may eventually appear in a natural database, it is highly unlikely that concatamers based on them will. The probability that such a sequence will arise and work with primers designed specifically for the barcode primers, and produce the proper sized amplicons, is extremely small. Even if this does occur, that sequence would have to be present in an evidentiary sample to be problematic (and sequencing the DNA from the sample would reveal this coincidence).

The exemplary nullomer barcode described herein is 120 bases long, and since only 1,900 copies are needed per PCR reaction, the additional cost to sampling kits would be minimal. A single 100-µg synthesis (less than $500) is sufficient for more than a million forensic tests. These barcodes could easily be added to FTA paper, liquid buffer, cotton swabs, or other components of human DNA sampling kits. While DNA has the power to free the wrongfully convicted, it can also be the route of forensic error as illustrated by a recent, highly publicized wrongful conviction and incarceration, due to mislabeling of DNA samples. As DNA sampling and archiving becomes routine, the public needs to be assured that their DNA is being properly collected, stored and interpreted, and the present invention provides such a safeguard.

The invention claimed is:

1. A method of authenticating or tracking a biological sample of a human or other species, comprising the steps of:
  obtaining one or more reference markers, each of said reference markers including at least one identified prime or nullomer of said human or other species which is an isolated and purified artificial oligonucleotide,
  wherein said one or more reference markers include at least nucleic acid oligomers of SEQ ID Nos. 101, 113, 132, 144, 193, 235, and 281;
  combining said biological sample with said one or more reference markers; and then
  determining if a test sample includes said one more reference markers, wherein if said test sample includes said one or more reference markers then said test sample is authenticated to be said biological sample, and if said test sample does not include said one or more reference markers then said test sample is determined to not be said biological sample.

2. The method of claim 1 wherein said biological sample is of a human.

3. The method of claim 1 wherein said biological sample is a forensic sample.

4. The method of claim 1 wherein said determining step includes amplifying said one or more reference markers.

5. The method of claim 4 wherein said amplifying is performed as part of a polymerase chain reaction.

6. The method of claim 1 wherein said one or more reference markers is associated with a detectable label.

7. The method of claim 1 wherein said detectable label is a fluorescent tag.

8. A method of determining the validity of a biological sample of a human or other species, comprising
  determining if a test sample includes one or more reference markers, wherein said one or more reference markers include at least nucleic acid oligomers of SEQ ID Nos. 101, 113, 132, 144, 193, 235, and 281, each of said reference markers including at least one identified prime or nullomer of said human or other species which is an isolated and purified artificial oligonucleotide, wherein if said test sample includes said one or more reference markers then said test sample is determined to be not a validly obtained biological sample, and if said test sample does not include said one or more reference markers then said test sample is determined to be a potentially validly obtained biological sample.

* * * * *